United States Patent
Hensel et al.

(10) Patent No.: US 9,235,744 B2
(45) Date of Patent: Jan. 12, 2016

(54) DEVICES FOR TRANSMITTING ITEMS OF INFORMATION OF OPTICAL BARCODES, OPTICAL BARCODES HAVING PHASE-SHIFTED CLOCK AND REFERENCE TRACKS, AND METHODS FOR CAPTURING OR TRANSMITTING INFORMATION OF SUCH OPTICAL BARCODES

(71) Applicant: Roche Diagnostics Operations, Inc., Indianapolis, IN (US)

(72) Inventors: Uwe Hensel, Viernheim, DE (US); Guenther Schmelzeisen-Redeker, Lorsch, DE (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 76 days.

(21) Appl. No.: 13/854,294

(22) Filed: Apr. 1, 2013

(65) Prior Publication Data
US 2013/0221090 A1    Aug. 29, 2013

Related U.S. Application Data

(63) Continuation of application No. PCT/EP2011/066993, filed on Sep. 29, 2011.

(30) Foreign Application Priority Data

Oct. 1, 2010 (EP) .................................... 10186031

(51) Int. Cl.
| | |
|---|---|
| G06K 7/10 | (2006.01) |
| G06K 7/14 | (2006.01) |
| G06K 19/06 | (2006.01) |
| G06F 17/30 | (2006.01) |
| G01N 35/00 | (2006.01) |

(52) U.S. Cl.
CPC .............. *G06K 7/1456* (2013.01); *G06F 17/30* (2013.01); *G06K 7/10722* (2013.01); *G06K 7/10762* (2013.01); *G06K 19/06028* (2013.01); *G01N 2035/00752* (2013.01); *G06K 2007/10504* (2013.01)

(58) Field of Classification Search
CPC ............ G06K 7/10762; G06K 7/0163; G06K 19/06131
USPC ................................................... 235/375, 494
See application file for complete search history.

(56) References Cited

U.S. PATENT DOCUMENTS 4,237,375 A * 12/1980 Granholm ...................... 235/487
4,806,741 A *  2/1989 Robertson ................... 235/462.1

(Continued)

FOREIGN PATENT DOCUMENTS

| | | | |
|---|---|---|---|
| EP | 0180283 A2 | 5/1986 |
| EP | 0379017 A2 | 7/1990 |
| EP | 0492326 A2 | 7/1992 |

*Primary Examiner* — Thien T Mai
*Assistant Examiner* — Toan Ly
(74) *Attorney, Agent, or Firm* — Roche Diabetes Care, Inc.

(57) ABSTRACT

A barcode reader for capturing a barcode connected to a moving carrier is proposed having at least one optical barcode detector for at least one-dimensional capture of information modules of the barcode. The barcode reader furthermore comprises at least one optical clock track detector for capturing clock track modules of a clock track of the barcode and at least one optical reference detector for capturing at least one item of reference information of the barcode. The barcode reader is configured to determine a direction of movement of the carrier from at least one signal from the clock track detector and at least one signal from the reference detector.

27 Claims, 24 Drawing Sheets

(56) References Cited

U.S. PATENT DOCUMENTS 5,164,574 A * 11/1992 Ujiie et al. ............... 235/462.05
5,992,743 A * 11/1999 Suemoto et al. ......... 235/462.05
2006/0163357 A1 * 7/2006 Kim et al. .................. 235/462.1
2006/0267753 A1 * 11/2006 Hussey et al. ................. 340/505
2009/0074618 A1 * 3/2009 Mizumoto et al. ........... 422/68.1

* cited by examiner

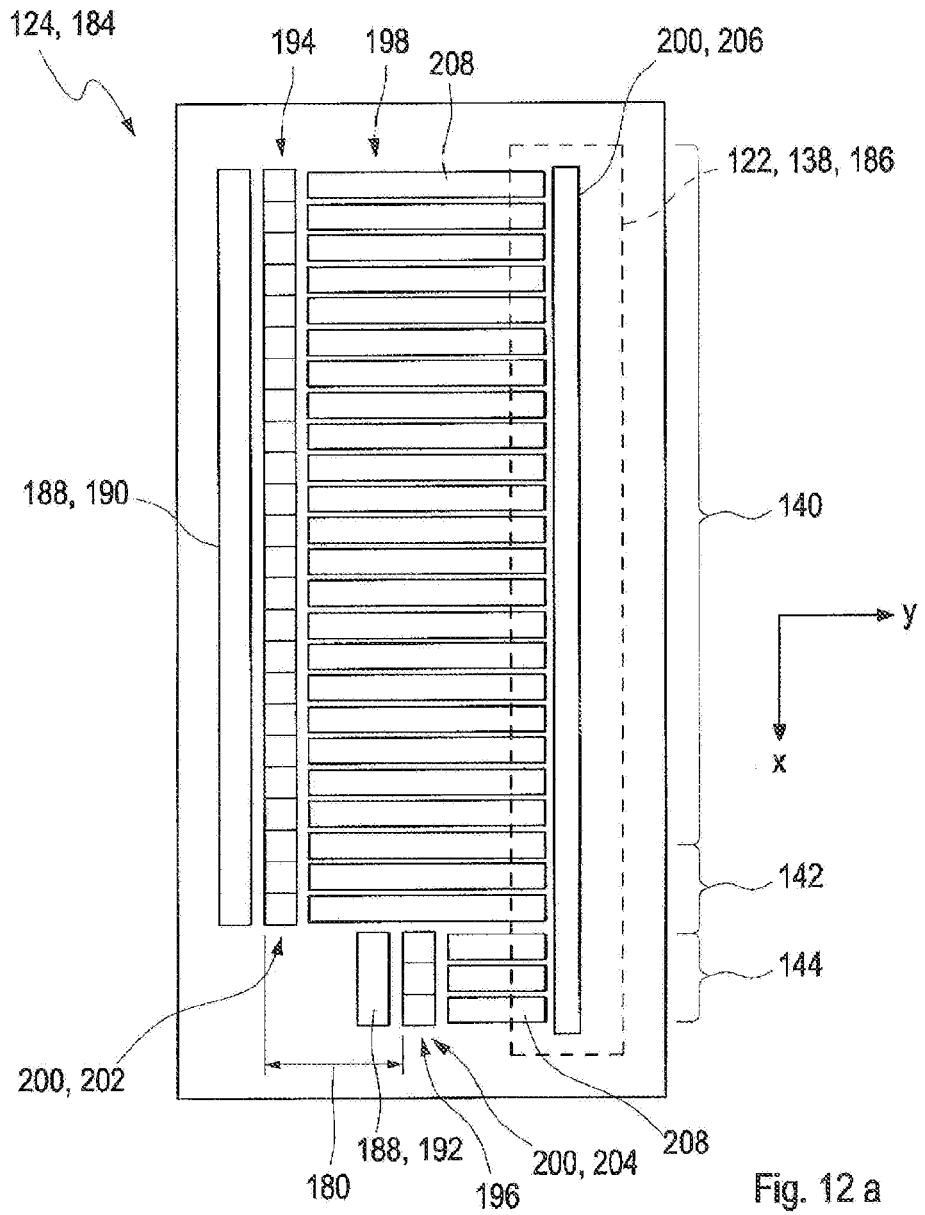
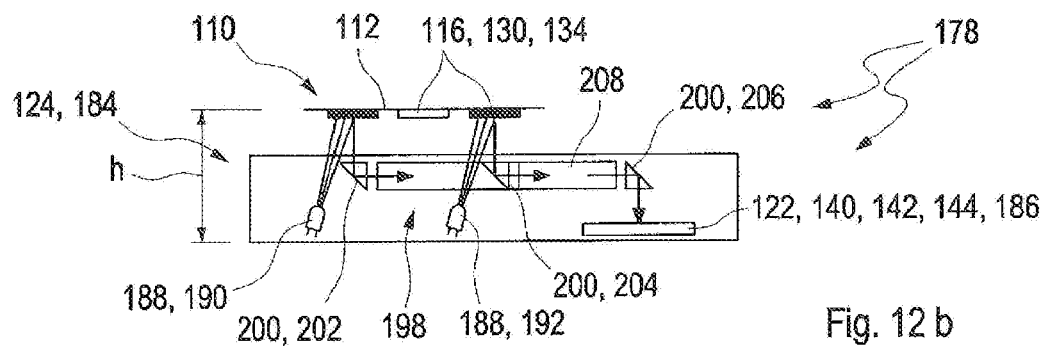
Fig. 12 a
Fig. 12 b

DEVICES FOR TRANSMITTING ITEMS OF INFORMATION OF OPTICAL BARCODES, OPTICAL BARCODES HAVING PHASE-SHIFTED CLOCK AND REFERENCE TRACKS, AND METHODS FOR CAPTURING OR TRANSMITTING INFORMATION OF SUCH OPTICAL BARCODES

CLAIM OF PRIORITY

The present application is a continuation application based on and claiming priority to PCT Application No. PCT/EP2011/066993 filed Sep. 29, 2011, which claims priority to European Patent Application No. EP 10186031.0, filed Oct. 1, 2010, each of which are hereby incorporated by reference in their respective entireties.

TECHNICAL FIELD OF THE INVENTION

The invention relates to a barcode reader for capturing an optical barcode connected to a moved carrier. The invention furthermore relates to a device for transmitting at least one item of information, comprising a barcode reader according to the invention and a carrier with an optical barcode. The invention furthermore relates to a barcode, in particular for marking a consumable article, more particularly an analytic test element for use in a device according to the invention, and to the use of the device for transmitting consumable-specific information from medical consumables to medical instruments. Finally, the invention relates to a method for capturing an optical barcode connected to a moved carrier. Such devices and methods can, in particular, be used in the field of medical diagnostics in order to transmit consumable-specific information from medical consumables, such as e.g. test strips, lancets, test elements or similar medical consumables, to medical instruments, for example to medical instruments configured to detect one or more analytes in a bodily fluid. However, in principle, other fields of application of the present invention are also feasible.

BACKGROUND

For the purpose of identifying specific products, or else for the purpose of data storage, in particular of small amounts of information, the prior art has widely disclosed the use of barcodes, for example one-dimensional or two-dimensional barcodes. By way of example, barcodes have been disclosed which are applied directly onto the products to be identified or marked, for example by means of appropriate printing techniques or else other techniques, for example laser techniques. However, as an alternative or in addition thereto, the barcodes can also be applied separately by means of appropriate adhesive techniques, for example by means of barcode labels.

Medical consumable articles are an important exemplary embodiment thereof; the present invention can, in particular, be related thereto but the present invention is not restricted thereto. Such medical consumable articles are used in medical diagnostics for example and can, for example, be embodied as disposable articles. Examples of such consumable articles are lancets for producing a puncture in an area of skin of a user, in particular for the purpose of generating a sample of a bodily fluid of the user. However, as an alternative or in addition thereto, the consumables can, for example, also comprise test elements, i.e. elements which are used to detect a property of a sample. By way of example, this property can be a concentration of one or more analytes in the bodily fluid. For this purpose, the consumables, which can for example be embodied as test strips, test tubes, test tapes or similar types of consumable articles, can in particular comprise one or more test fields. As a rule, these test fields comprise one or more test chemicals which specifically change at least one detectable property if the analyte to be detected is present. By way of example, this can be a property which can be detected electrochemically or optically, such as, for example, a color change. In principle, such test elements are known from the prior art. By way of example, these test elements can be used for qualitative and/or quantitative detection of blood glucose, lactate, cholesterol, coagulation values or similar parameters in the sample.

In the case of medical consumable articles, particularly in the field of medical diagnostics, at least one item of information in respect of the consumable article must, in general, be read into a medical instrument interacting with the consumable article. According to the prior art, this is generally performed manually or via electronic transmission methods, such as, for example, so-called ROM keys, which are added to packaging of the consumables and are entered into the medical instrument when the consumables are used for the first time. However, in principle, other forms of data transmission are also possible. By way of example, the transmitted data can contain information in respect of how the medical instrument interacts with the consumable articles and/or how the consumable articles are to be used. By way of example, this can be calibration information, batch-specific data or similar data since test strips, for example, usually have properties which differ from batch to batch and should be taken into account when using the consumable articles and more particularly when evaluating measured values which were obtained using these consumable articles.

The prior art has disclosed a number of different types of barcodes. Here, these can be simple one-dimensional barcodes, which are also referred to as linear barcodes, or, as an alternative or in addition thereto, else be multidimensional barcodes, for example so-called data matrix codes. Various options will be explained in more detail below.

Barcodes are usually read by means of hand-guided or motor-driven swipe systems or by means of moved mirror-deflected laser beams (scanners). Such reader systems are typically used in the case of one-dimensional barcodes. In the case of two-dimensional or multidimensional barcodes, which comprise significantly more information, use is generally made of camera systems or else mirror scanners. The use of CCD row-systems by moving the objects and goods past the CCD row in motor-driven and perpendicular fashion is also known, particularly in production processes and/or assembly-line methods. In order to decode and read out the information of these partial images of multidimensional barcodes, supplied by means of camera systems or, for example, CCD rows, high demands must generally be placed on both the motion sequence of the scanner or the moving past of the articles and on the utilized computer systems. In particular, use must generally be made of high-speed computer systems. In order to enable spatial resolution of the submodules, i.e. the binary information carriers, contained in the barcode, use is made of speed information contained in the code in the form of relative defined distances of the submodules in the case of one-dimensional barcodes or of clock tracks in the case of two-dimensional barcodes. Such barcodes are also referred to as "self-clocked barcodes". However, all previously used barcodes assume a precise unidirectionality of the movement process, within the scope of which the article with the barcode is moved past the barcode reader. Although a violation of the unidirectionality is often identified in the case of one-dimensional barcodes, if such a so-called "bad scan" is identified, this generally requires a new scanning attempt. Mirror-guided or camera-supported scan systems in the case of two-dimensional barcodes often automatically ensure speed constancy and unidirectionality.

From prior disclosure it is known to provide a reader for moved-past transport goods or containers provided with a data medium. The reader comprises a reader head which can scan information present in an information track of the data medium. Provision is furthermore made for a clock track, which is scanned by means of two sensors. The two sensors are arranged offset with respect to one another. This arrangement can be used, inter alia, to identify a movement direction of the barcode and, accordingly, to read out information content into a shift register. See, e.g., EP 0 180 283 A2

It is also known to provide an apparatus for identifying objects moved along a track. By way of example, these can be transport cars which are provided with an information carrier. The information carrier comprises three rows of holes. Here, an upper row and a lower row serve as information rows, in which the encoded information is present. The upper and lower rows complement one another, and so respectively one hole is made in the holes of the rows lying above one another. By way of example, if the upper hole is present, this means that there is a 1 at this place of the binary number to be represented, while a hole in the lower row represents a 0. By contrast, the central row is embodied such that all holes are present therein, respectively independently of the respective information. The markings in the second row are arranged offset compared to the markings in the first and the third row. Respectively one row is associated with a scanning element which is arranged in a spatially fixed manner. Furthermore, a corresponding algorithm for identifying the information is described. Inter alia, edge identification is also disclosed herein. See, e.g., EP 0 379 017 A2.

It is also known to provide a test carrier analysis system for analyzing a constituent of a bodily fluid. Inter alia, provision is made in this case for a test carrier and a code carrier. See, e.g., EP 0 492 326 A2.

However, both motor-operated barcode readers and manually operated barcode readers can still lead to irregular conditions, in which the demands in respect of speed constancy and unidirectionality are violated. By way of example, mechanical resistances can occur in the case of motor-operated barcode readers and these may lead to jerks in the drive systems. If the transport direction is violated, bad scans can also occur in this case. Although manually operated barcode readers, in which the articles provided with the barcode are guided past the barcode reader manually, are comparatively stable with respect to speed constancy, a shaking operator of the system would, under certain circumstances, also fail to meet a demand in respect of unidirectionality.

It is therefore an object of the present invention to provide methods and devices which at least largely avoid the disadvantages of the above-described, known methods and devices. In particular, a barcode reader, in particular for use in a medical instrument, is to be proposed, which can be realized easily and with a small installation space and which can also be used reliably in manually guided applications.

SUMMARY

This object and others that will be appreciated by a person of ordinary skill in the art have been achieved according to the embodiments of the present invention disclosed herein. In one embodiment, the present invention comprises a barcode reader for capturing a barcode connected to a moved carrier. Here, a barcode refers in general terms to an information carrier which can be read out by optical or optoelectronic means and which has a plurality of optically detectable modules which can assume at least two different optically detectable states. Here, a module is respectively understood to mean a two-dimensional or three-dimensional region of the barcode, the optically perceivable properties of which can assume the at least two states which can be distinguished from one another. By way of example, this can relate to defined two-dimensional regions on a surface of the carrier, or else to three-dimensional regions within a material of the carrier. Important examples, to which, however, the application is not restricted, are so-called linear codes or line codes, i.e. one-dimensional barcodes in which the modules consist of a sequence of rows which can assume at least two different values (e.g. "white" and "black"). As an alternative or in addition thereto, use can also be made of two-dimensional barcodes, for example so-called data matrix codes, in which modules are applied in two directions and for example arranged to form a matrix. In this case, the modules can for example be embodied as squares or rectangles. However, in principle, other embodiments are also possible. In respect of possible barcodes, reference can be made, for example, to conventional commercial barcodes according to the EAN (European Article Number), UPC (Universal Product Code) or similar codes. Other known standards for barcodes are also applicable. In respect of two-dimensional barcodes, reference can be made, for example, to data matrix codes, QR codes, codes according to the PDF standard or similar codes. Here, use can be made of two-dimensional codes with orthogonal coordinate systems or else, for example, with coordinate systems with polar coordinates. The modules are the smallest unit of information of the barcodes. Here, the modules are to be understood to mean an area or a space of the overall region of the barcode, which can assume the at least two optically detectable states. In the case of binary barcodes, these at least two states can be binary, i.e. a first state or a second state can be assumed. However, in principle, other embodiments are also possible, i.e. embodiments in which more than two states are possible, which, for example, can be realized within the scope of so-called grayscale codes.

The optically perceivable property which can assume the at least two states can be one of different types of optical properties. By way of example, this can be a reflectivity, a color, fluorescence, transparency or another type of optical properties or a combination of the aforementioned and/or other properties. This optically perceivable property, which can assume the at least two states, can for example be directly introduced into the carrier, for example into a material and/or onto a surface of the carrier, or can, as an additional marking material, for example be applied to the carrier. As an example of this, reference should be made to printing a color onto a surface of the carrier, as a result of which e.g. the reflectivity and/or the transparency of the carrier surface and/or a fluorescent property of the carrier surface are changed. By way of example, this additional marking material can be printed, sprayed or dripped onto the carrier or else applied to the carrier by means of a separate carrier element, e.g. an adhesive film. Alternatively, it is also possible to modify the carrier itself, for example by irradiation, for example by means of a laser, by means of which the barcode is applied onto or introduced into the carrier directly or, in turn, onto or into a marking material connected to the carrier. Various embodiments are possible.

In principle, the carrier can be any carrier. In one embodiment, the carrier comprises a medical consumable article or part of a medical consumable article or connected to a medical consumable article. Here, in principle, a medical consumable article is to be understood to mean any article which is required within the scope of medicine or medical engineering, in particular as an aid, for example for therapy and/or diagnostics. Here, in principle, this can for example be a diagnostic and/or therapeutic aid and/or packaging of such an aid which itself can be denoted as a consumable article. Without excluding other possible types of consumables, reference should be made here to diagnostic aids in particular, for example test elements such as test strips, test tapes, lances or the like. By way of example, these can be individual test strips which are configured to analyze at least one property of a sample, for example in order to carry out a qualitative and/or quantitative detection of at least one analyte in a sample of a bodily fluid. In this respect, reference can be made, for example, to known optical and/or electrochemical test strips. Various exemplary embodiments will be mentioned in more detail below.

Within the scope of the present invention, a barcode reader may, in general, be understood to comprise a device which is configured to read out the barcode at least to the extent that the information from the barcode is converted into electric signals or storage states of a data storage of the barcode reader. Accordingly, the barcode reader has at least one device which is configured to capture the properties of the modules of the barcode, which can assume the at least two states, in a qualitative or quantitative fashion. By way of example, as will be explained in more detail below, these devices can be devices with an optical emitter for emitting at least one least one kind of electromagnetic radiation, such as light in the visible and/or infrared and/or ultraviolet spectral range, and/or an optical detector for receiving electromagnetic radiation, once again such as light in the infrared and/or visible and/or ultraviolet spectral range. In general, an "optical" property within the scope of the present invention should be understood to mean a property which can be perceived by means of electromagnetic radiation, such as light in the visible and/or ultraviolet and/or infrared spectral range or which is based on such light.

The proposed barcode reader has at least one optical barcode detector for at least one-dimensional capture of information modules of the barcode. In other words, the barcode should comprise a plurality of information modules which can be captured by means of at least one optical barcode detector of the barcode reader. Here, information modules of the barcode are understood to mean the actual information carriers of the barcode, in which the information of the barcode is stored in encoded form. By way of example, the barcode detector, as will be explained in more detail below in an exemplary fashion, and also, optionally, the other detectors of the barcode reader, which are yet to be explained in more detail, can comprise at least one optically sensitive element, for example a photodiode, a photocell, a CCD chip, a phototransistor or similar optically sensitive elements which can, for example, detect an intensity or changes in an intensity of incident electromagnetic radiation, more particularly of light in the visible and/or infrared and/or ultraviolet spectral range. In the process, the detectors can comprise one or more optically sensitive elements. By way of example, as will be explained in more detail below, use can be made of one-dimensional detector rows with a plurality of optically sensitive elements or optically sensitive surfaces arranged in a row, e.g. CCD rows. In principle, two-dimensional arrays are also possible and, in principle, other embodiments of the detectors as well.

Here, at least one-dimensional capture of information modules of the barcode should be understood to mean that, in the case of movement of the barcode relative to the barcode reader, at least one detector of the barcode detector successively records information in a temporal sequence, including a plurality of detectors doing this simultaneously, for example sensitive elements from a detector row or a detector array such as, for example, a detector matrix of the barcode detector.

The barcode reader furthermore comprises at least one optical clock track detector for capturing clock track modules of a clock track of the barcode. Here, a track should be understood to mean a plurality of successive modules, which are arranged successively along a straight or else curved line in the barcode and which typically do not simultaneously serve as information modules of the barcode but which may only serve for clocking when the barcode is moved relative to the barcode reader. Here, clocking is understood to mean a synchronization of currently read out information from the barcode reader, which is currently being read out from the information modules, with a spatial arrangement within the barcode, for example row-by-row further cycling for assigning row information to a specific row of the barcode, for example within a storage of the barcode reader.

The barcode reader furthermore has at least one optical reference detector for capturing at least one item of reference information from the barcode. The barcode reader is configured, for example by means of an appropriate evaluation device, to deduce a movement direction of the carrier from at least one signal from the clock track detector and at least one signal from the reference detector. By way of example, provision can be made for an evaluation device which compares current signals from the clock track detector with signals from the reference detector and deduces a movement direction of the carrier in accordance with the possible cases that can occur. Thus, for example, a movement can be deduced in general terms from a signal from the clock track detector, more particularly from a change in a signal level from the clock track detector, from which in turn it is possible, for example, to deduce further cycling of information currently read out by the barcode detector and/or wherein further cycling can be triggered, for example for the purpose of clocked data storage. From the additional information from the reference detector it is then furthermore possible, particularly in conjunction with the signal from the clock track detector, to deduce whether the further cycling took place or should take place in a positive or negative direction. By way of example, this signal evaluation can be implemented using appropriate electronics, for example by means of comparison electronics and/or an electronic table and/or one or more discriminators. As an alternative or in addition thereto, the optional evaluation device can also, for example, comprise a data processing device, which can process and evaluate the signals, in particular the current signals, from the clock track detector and/or the reference detector or else secondary signals derived from these signals. In particular, the evaluation device can be configured to read out and/or at least partly evaluate the signals from the clock track detector and/or the reference detector, in particular the current signals, or secondary signals derived from these signals, by means of at least one data-processing algorithm.

The barcode reader can, in particular, be configured to capture at least one signal change caused by the clock track in the signal from the clock track detector, more particularly a positive or negative edge in an optical and/or electric signal. By way of example, this can be brought about by differentiating the signal from the clock track detector, which is for example compared to one or more thresholds. Such edge detectors are well known from the field of electronics. By way of example, a sign of the edge can also be identified in this fashion. By way of example, in the case of a binary black/ white barcodes, such edges occur at the transition from a black module to a white module (positive edge in a reflection signal) or vice versa (negative edge in a reflection signal).

Here, the typically coincident signals from the clock track detector and from the reference detector are compared to one another in order to deduce a movement direction of the carrier therefrom. Here, within the scope of the present invention, coincident signals should be understood to mean signals that are recorded simultaneously. In addition to absolute simultaneity, tolerances are also possible in this case, for example deviations with an absolute temporal value which is typically no more than 200 µs, particularly no more than 100 µs and more typically no more than 50 µs.

The barcode reader can more particularly be configured to deduce the movement direction of the carrier relative to the barcode reader from a sign of a signal change captured by the clock track detector and from an absolute value of the signal from the reference detector, more particularly from a coincident signal from the reference detector. By way of example, if binary information is present in the modules, four different cases can, in principle, occur: thus, for example, there can be a positive edge in the signal level of the signal from the reference detector, paired with a positive signal level ("white" or "1") or paired with a negative signal level ("black" or "0"). Alternatively, a negative edge can also occur in the signal from the clock track detector, paired with positive or negative signals in the absolute value of the signal from the reference detector. By way of example, of these four possibilities, respectively two can correspond to a first movement direction of the carrier relative to the barcode reader, and the other two can correspond to a second movement direction, for example to an opposite movement direction. By way of example, this can be realized by virtue of the reference detector recording signals which, when the barcode moves relative to the barcode reader, have a periodicity which is phased-shifted compared to a periodicity of the signals from the clock track detector. By way of example, this phase shift can be realized by virtue of the fact that, as will be explained in more detail below, the clock track detector records signals of the clock track itself, which are shifted by a phase of or in position space, for example by virtue of the reference detector being spatially offset by a corresponding distance (for example parallel to the movement direction) compared to the clock track detector and/or by virtue of the fact that a separate reference track of the barcode is measured, which has the same periodicity (or an integer multiple thereof) as the clock track itself but is phase-shifted with respect to the clock track by a phase offset deviating from with respect to a module height H of the modules in the movement direction. The at least one optional reference track is typically aligned parallel to the at least one clock track, for example by virtue of the reference track and the clock track both being aligned parallel to the movement direction. Examples will be explained in more detail below.

Accordingly, the barcode reader can for example be configured to perform the following steps: deducing a first movement direction if a negative edge is identified in the signal from the clock track detector and a first signal level is identified in the signal from the reference detector or if a positive edge is identified in the signal from the clock track detector and a second signal level is identified in the signal from the reference detector; and deducing a second movement direction in the opposite direction to the first movement direction if a positive edge is identified in the signal from the clock track detector and the first signal level is identified in the signal from the reference detector or if a negative edge is identified in the signal from the clock track detector and the second signal level is identified in the signal from the reference detector.

The movement direction can be used, in particular, to bring about further cycling when storing the information read out from the information modules of the barcode. Thus, the barcode reader can, for example, comprise a data storage, wherein the barcode reader is configured to read out information contained in rows of the barcode and store it in the data storage, respectively with an address counter corresponding to the row. In particular, the barcode reader can be configured to increase or decrease the address counter incrementally in accordance with the identified movement direction. Such embodiments are typical in the case of one-dimensional barcodes (in this case a row of the data storage contains precisely one value) or in the case of two-dimensional, rectangular barcodes (in this case a row of the data storage contains a plurality of items of information, corresponding to the number of modules in one row of the barcode). By way of example, the barcode can have a rectangular field of matrix-shaped modules, with, for example, an intended movement direction of the barcode or of the carrier relative to the barcode reader defining a y-direction and a direction perpendicular to this intended movement direction defining an x-direction. A row of the barcode then is the set of information modules of the barcode which have the same y-coordinate. Thus, the rectangular field may be aligned with one side parallel to the intended movement direction. As will be described in more detail below, the true movement direction or the actual movement direction can deviate from the intended movement direction, with, however, the barcode reader in one embodiment being configured such that the deviation is no more than 20°, in particular no more than 10°, typically no more than 5°. In this respect, without restricting further possible embodiments, no distinction is made anymore in the following description between the intended movement direction and the actual movement direction, and the assumption is made that the y-axis is aligned parallel to the movement direction. If deviations in the movement direction are described, this means angle deviations between the actual movement direction and the intended movement direction.

Furthermore, the expression "in the movement direction" is, in principle, understood to mean a direction parallel to the movement direction. However, within the scope of the present invention, a deduction in respect of a movement direction can in particular be understood to mean a deduction in respect of a sign of the movement, i.e. information in respect of whether the movement is in the positive or negative y-direction. By way of example, this sign allows deductions to be made in respect of an incremental increase or decrease to be undertaken in respect of address information, as will be explained in more detail below.

The optical clock track detector can be embodied as a separate clock track detector, which is different from the barcode detector. However, as an alternative or in addition thereto, the clock track detector can also be wholly or partly part of the barcode detector, i.e. be contained in the barcode detector. Thus, for example, part of the barcode detector can be used as clock track detector. An analogous statement also applies to the reference detector, which likewise can be embodied as a separate detector. However, alternatively, the reference detector can, in turn, also be wholly or partly part of the bar-code detector, for example by virtue of part of the barcode detector being used as reference detector. However, the clock track detector and the reference detector can also be separate detectors, which are arranged offset with respect to one another. In particular, the reference detector can be arranged next to the clock track detector in a direction perpendicular to the movement direction.

This embodiment is particularly expedient if use is made of barcodes which, as will be explained in more detail below, aligned parallel to the movement direction, next to the at least one clock track, comprise at least one reference track which can be used as direction track and which can be read out separately by the reference detector. As explained above, this reference track can, for example, be a second clock track which, for example, has the same periodicity as the clock track but has a phase offset compared to the clock track. Here, a "second clock track" should be understood to mean a track which is embodied in the same fashion as the at least one track actually used as clock track, wherein, however, this at least one additional track is not used as clock track but rather as reference track. Ultimately, the barcode can in this case be embodied in such a way that the latter comprises at least two clock tracks, wherein at least one of the at least two clock tracks can be or is used as actual clock track for clocking and wherein at least one further one of the at least two clock tracks can be or is used as reference track. However, in principle, other embodiments are also possible. As an alternative to an embodiment of the reference detector next to the clock track detector with an offset perpendicular to the movement direction, or in addition thereto, an embodiment of the reference detector is also possible, in which it is arranged offset compared to the clock track detector in a direction parallel to the movement direction. In particular, there can be an offset by a positive or negative value Δ, wherein the offset Δ deviates from an integer multiple of a module height of the modules of the barcode in the movement direction. In particular, it is possible to select an offset which corresponds to a non-even multiple of half a module height of the clock track modules and/or reference track modules in the movement direction. The latter embodiment of a reference detector offset in the movement direction can be selected, in particular, if use is made of merely one clock track. In this case, the reference detector can read out the same clock track in position space with a phase offset, wherein the phase offset typically deviates from an integer multiple of 2·H. In this case too, it is possible to deduce a movement direction from e.g. an edge signal from the clock track detector and an absolute signal level from the reference detector. The spatial offset typically deviates from an even multiple of half a module height.

In accordance with this possible embodiment, the optical reference information from the barcode, which is read out by the reference detector, can be embodied in a number of ways. Thus, for example, optical information from a reference track of the barcode can be selected as optical reference information, i.e., for example, an optical property of the reference track locally present at the point of the reference detector (or at the points of the reference detectors in the case of a plurality of reference detectors). However, as an alternative or in addition thereto, it is also possible, as explained above, for the at least one clock track of the barcode to be read out. Thus, optical information from the clock track of the barcode at a predetermined offset with respect to optical information from the clock track currently read out by the clock track detector can be used as optical information from the reference track. In particular, in the process it is possible to select an offset in a direction parallel to the movement direction of the carrier relative to the barcode reader, in particular an offset deviating from an integer multiple of a module height of the clock track.

As illustrated above, the carrier can be embodied in various ways. By way of example, this carrier can itself be a consumable article, can be part of a consumable article or can be connected to a consumable article. However, in principle, other embodiments are also possible. Here, it is expedient in many cases if the barcode reader itself comprises a receptacle which is configured to receive the carrier wholly or partly. In particular, this can be a slot into which the carrier can be wholly or partly inserted, a guide rail into which the carrier can be wholly or partly inserted or another type of receptacle. In particular, the receptacle can be configured to enable movement of the carrier in the receptacle, for example movement merely in a direction parallel to the movement direction. However, slight angle tolerances are also possible in principle here, for example angle tolerances of no more than 20°, in particular no more than 10° and typically of no more than 5° or even 3° or less. Such tolerances can be achieved without problems using conventional guide rails or slots, particularly in the case where the carrier is optionally embodied in a strip-shaped manner, for example as test strip with a barcode. In particular, the receptacle can be configured in such a way that the carrier can be moved in the receptacle, including by hand. Accordingly, the receptacle can, for example, have a purely passive embodiment, i.e. without actuators which would actively bring about movement of the carrier relative to the barcode reader. By way of example, this can be brought about in the form of a slot or a guide rail, which is embodied in such a way that manual access to the carrier in the receptacle is still possible. However, as an alternative to a pure movability by hand, provision could just as well be made for one or more actuators in another embodiment, said actuators actively bringing about a movement of the carrier relative to the barcode reader. By way of example, the barcode reader can be wholly or partly embodied as a scanner, wherein a manual or automatic relative movement of the carrier and of the barcode reader or of part thereof, for example the barcode can be moved over the barcode detector, or vice versa, allows the barcode to be read out.

Thus, in principle, the receptacle is configured to enable movement of the carrier relative to the barcode reader. This movement may occur in one dimension, wherein, however, other movements are just as well also possible. There typically is a linear movement along a straight movement direction, i.e. an intended movement direction. However, in principle, curved movements are also possible.

In general, reference should be made in this respect to the fact that movement of the carrier relative to the barcode reader can more particularly comprise a movement of the carrier and hence of the barcode relative to the barcode detector. Here, a relative movement of the carrier relative to the barcode reader should be understood to mean a movement in at least one coordinate system, for example in a coordinate system in which the carrier and/or the barcode are at rest, or in a coordinate system in which the barcode reader or part thereof, for example the barcode decoder, is at rest, or in a coordinate system in which both the carrier and the barcode reader are moving. Thus, the relative movement can be embodied such that the carrier and/or the barcode move while the barcode reader or part thereof, e.g. the barcode detector, is at rest. Alternatively, the relative movement can also be embodied such that the carrier and/or the barcode are at rest while the barcode reader or part thereof, e.g. the barcode detector, is moving. In another alternative, the relative movement can also be embodied such that both the carrier and/or the barcode, and also the barcode reader or part thereof, e.g. the barcode detector, are moving, wherein, for example, a spacing between the barcode and the barcode reader and/or the barcode detector can be modified by the movement.

The barcode reader may be configured in such a way that the barcode can be read out by means of the barcode reader while the carrier moves in the receptacle.

The readout can be initiated by, for example, a user, for example by actuating at least one button or switch or else another type of actuation element. Alternatively, or in addition thereto, the readout can also be initiated automatically, for example when the carrier with the barcode is inserted, e.g. pushed, into a receptacle. By way of example, the receptacle can have at least one switch, with the switch being actuated by the carrier and/or a test element comprising the carrier during the insertion or after the insertion. By way of example, this actuation can initiate the relative movement and/or the readout of the bar-code.

Further possible embodiments of the proposed barcode reader relate to the embodiment of the various detectors. In particular, one or more of the detectors, i.e. the barcode detector, the clock track detector or the reference track detector or any combination of these detectors, can be embodied such that these, in pairs or all together, resort to one or more common optical sensor elements. Thus, for example, the barcode reader can comprise at least one optical sensor element, for example a sensor row, in particular a CCD row, wherein the clock track detector and the reference detector are configured to use the optical sensor element. By way of example, the clock track detector can use a first section of a sensor row, for example of a CCD row, and the reference detector can use a further section. Furthermore, the barcode detector can optionally also use a section of this sensor row. Various embodiments are possible. The common use of an optical sensor element by a plurality of the detectors of the barcode reader can for example be brought about by suitable optical deflection elements, such as, for example, one or more mirrors, prisms or similar deflection elements, such that, for example, optical signals can accordingly be directed at the sensor element.

In addition to the barcode reader according to one or more of the above-described embodiments, a device is furthermore proposed for transmitting at least one item of information, comprising at least one barcode reader as per one or more of the above-described embodiments. The device furthermore comprises at least one carrier with at least one barcode, said carrier for example having the above-described features relating to the carrier. By way of example, this barcode can be a barcode with the above-described features relating to the barcode.

The barcode comprises a plurality of information modules and at least one clock track. In respect of the possible embodiments of the clock track, reference can be made to the description above. As will be explained in more detail below, the barcode can additionally comprise at least one reference track, or the clock track itself can, as explained above, be simultaneously used as reference track. Here, at least one "additional" reference track should be understood to mean at least one reference track which is embodied separately from the at least one clock track. By way of example, the at least one reference track can extend next to the at least one clock track, wherein the reference track can, for example, directly adjoin the at least one clock track or else be embodied separately from the at least one clock track, for example as a result of a spacing. In particular, the at least one reference track can extend parallel to the at least one clock track. By way of example, the at least one optional reference track can have a parallel offset with respect to the at least one clock track. Furthermore, the at least one reference track can have the same periodicity as the at least one clock track. The at least one reference track may, for example, have a periodicity which is phase-shifted compared to a periodicity of the at least one clock track.

The device is optionally configured in such a way that the carrier can be moved by hand relative to the barcode reader in at least one movement direction. To this end, the device can for example, as explained above, comprise at least one receptacle for receiving the carrier. In respect of the possible embodiments of the receptacle, reference can be made to the description above. In particular, the receptacle can be configured such that manual movement of the carrier relative to the barcode reader is made possible. However, in principle, other embodiments are also possible.

The carrier can, in particular, be a medical consumable article, part of a medical consumable article or a carrier element connected to a medical consumable article. In particular, this can be an analytic test element, for example a test strip, for detecting at least one analyte in a bodily fluid. However, other embodiments are also possible, in particular the embodiments described above.

The clock track can more particularly be arranged parallel to the movement direction, i.e. to the intended movement direction. The clock track can more particularly have a plurality of periodically alternating clock track modules, wherein the alternating clock track modules are configured to produce at least two different signal levels alternately in the clock track detector when passing the clock track detector. A repetition frequency of the clock track modules in the movement direction can, in particular, correspond to a repetition frequency of the information modules of the barcode in the movement direction. In other words, the module height and/or a module pitch in the movement direction can for example correspond for the clock track and the information modules of the barcode. If an additional reference track is present, the latter can also have the same repetition frequency as the clock track and/or the information modules of the barcode. However, in principle, other embodiments are generally also possible, for example by virtue of the clock track having a repetition frequency in the movement direction which is an integer multiple of the repetition frequency of the information modules of the barcode, or the like.

In particular, the barcode can be embodied such that the information modules are arranged in at least one information field of the barcode. By way of example, this information field can be embodied as rectangular field with rows and columns of information modules, with the columns, for example, being aligned parallel to the movement direction. However, in principle, other embodiments are also possible. The clock track can then be embodied separately from the information field, for example, separated from the information field, or else it can also be wholly or partly contained in the information field. In particular, an edge column of the information field, parallel to the movement direction, can also be used as clock track.

As an alternative to the use of at least one edge column of the information field as clock track and/or as optional reference track, or in addition thereto, the clock track and/or the optional reference track can also be moved into the interior of the barcode. Thus, for example, the clock track and/or the reference track can be embodied such that at least one column with information modules of the information field respectively adjoins perpendicular to the movement direction on both sides. In particular, the clock track and/or the reference track can be arranged in a central column of the barcode, or in a column of the barcode which may be arranged no more than five and typically no more than two module widths from the center of the barcode. As will be explained in more detail below, the arrangement of the clock track and/or the reference track in the interior of the barcode, such as in the center of the barcode, offers the advantage of a greater robustness in the case of an angle offset of the barcode relative to the movement direction.

Furthermore, the information field can optionally be embodied such that the latter comprises at least one edge row and/or at least one edge column, with the modules of the edge row and/or edge column being configured for producing a uniform signal level in the barcode reader. By way of example, use can be made of a purely white or purely black edge row and a purely white or a purely black edge column. These edge rows or edge columns can, firstly, be used as start/stop signals or else for calibrating signal levels.

As explained above, the barcode can furthermore have at least one reference track, which is embodied separately from the clock track. The reference track is also typically arranged parallel to the movement direction. By way of example, the reference track can have a plurality of periodically alternating reference track modules, with the alternating reference track modules being configured to produce at least two different signal levels alternately in the reference detector when passing the reference detector. Here, the periodicity of the reference track can be such that the former has the same repetition frequency as the clock track. However, the periodicity of the reference track should be phase-shifted compared to the periodicity of the clock track, such as by a non-even multiple of H/2.

The modules of the barcode, i.e. the information modules and/or the modules of the clock track and/or the modules of the optional reference track, can in general have a module height in the movement direction and a module width perpendicular to the movement direction. By way of example, the modules of the barcode and/or the modules of the optional reference track and/or the modules of the clock track can have a rectangular form, with the side length of the rectangles in the movement direction being the module height and with the side length of the rectangles perpendicular to the movement direction being the module width. The rectangles can be square or else not be square.

The module height of the modules of the barcode, i.e. of one or more of the modules selected from the group consisting of the information modules, the modules of the clock track and the modules of the reference track, can equal the module width but can, however, more particularly also exceed the module width, typically by at least a factor of 1.2, more particularly by at least a factor of 1.5 or even by a factor of 2. As will be explained in more detail below, this elongate embodiment of the modules also renders it possible to tolerate a tilt of the intended movement direction with respect to the actual movement direction, for example as a result of a barcode applied with tilt on the carrier and/or as a result of a tilt in the movement direction of a relative movement between carrier and barcode reader with respect to the columns of the barcode or with respect to the clock track and/or reference track, because, despite the tilt, it is still possible to ensure that, in the case of row-by-row readout, there still is a reading process in the same row despite the tilt.

In addition to the above-described barcode reader and the above-described device in one or more of the illustrated optional embodiments, a barcode is furthermore proposed. The barcode can more particularly be part of a consumable article, more particularly a medical consumable article. Accordingly, such a consumable article with at least one carrier and at least one barcode according to the invention can itself be subject matter of the present invention. In particular, the consumable article can be an analytic test element for detecting at least one analyte in a bodily fluid. By way of example, the analytic test element comprises at least one test chemical for detecting the analyte. Here, a test chemical should be understood to mean a substance which, if the at least one analyte to be detected is present, specifically changes at least one detectable property, for example a physically and/or chemically detectable property, more particularly an electrochemically and/or optically detectable property. The analytic test element more particularly comprises at least one carrier, for example a strip-shaped or tape-shaped carrier, and at least one barcode connected to the carrier. The analytic test element is typically configured to be used in a device as per one or more of the above-described embodiments.

The barcode comprises a plurality of information modules. The barcode furthermore comprises at least one clock track for clocking a readout of the information modules by means of at least one barcode reader. There is a relative movement between the barcode and the barcode reader in a movement direction. This relative movement can be carried out in such a way that, in principle, one or both of the barcode and barcode reader elements can move, i.e. the barcode, the barcode reader or the barcode and the barcode reader. Here, clocking should be understood to mean assigning at least one currently read out signal due to the information modules, for example from a barcode detector, to a spatial information in a movement direction, for example in the form of an address counter. The barcode furthermore comprises at least one reference track which is embodied separately from the clock track. The reference track has a phase offset compared to the clock track. In respect of the further possible embodiments of the barcode according to the invention, reference can be made to the description above. Accordingly, the barcode can for example have at least one clock track with the above-described features and optionally additionally have at least one reference track. Reference can be made to the description above in respect of further possible embodiments.

Accordingly, a consumable article is proposed in a further aspect of the present invention, which consumable article can, in particular, be embodied as medical consumable article. In particular, this can be a medical consumable article as per the description above. Hence, the consumable article can, in principle, comprise any articles which can be marked by a barcode. The consumable article comprises at least one carrier and at least one barcode, for example as per the description above, connected to the carrier. The barcode comprises a plurality of information modules. The barcode furthermore comprises at least one clock track for clocking a readout of the information modules by means of a barcode reader moved relative to the barcode in a movement direction. By way of example, this can be a barcode reader as per one or more of the embodiments described above. The barcode furthermore comprises at least one reference track which is embodied separately from the clock track, wherein the reference track has a phase offset compared to the clock track. In respect of further possible embodiments of the clock track, the reference track or further parts of the barcode, reference can be made to the description above.

In addition to the barcode reader presented above, the described device and the analytic test element, the use of a device as per one of the above-described embodiments is furthermore proposed for transmitting consumable article-specific information from at least one medical consumable article to a medical instrument interacting with the medical consumable article, more particularly to a medical measuring instrument and/or therapy instrument. Here, consumable article-specific information should be understood to mean information which characterizes at least one property of the medical consumable article. In particular, this can be batch-specific information, which should, for example, be used for evaluating a measurement carried out by means of the medical consumable article and/or which relates to an envisaged use of the consumable article. However, as an alternative or in addition thereto, the consumable article-specific information can also comprise information in respect of a type or at least one other property of the consumable article, for example a producer, a dose, an expiry date, a type of the medical consumable article or other types of information or combinations of the aforementioned and/or other information. The medical measuring instrument can, in particular, be a measuring instrument which is configured to capture qualitatively and/or quantitatively at least one body state of a user and/or at least one state of a sample. In particular, this can be a diagnostic measuring instrument, which is configured to detect at least one analyte qualitatively or quantitatively in a sample, more particularly a sample of a bodily fluid. By way of example, the at least one analyte can be at least one metabolite. However, as an alternative or in addition thereto, the medical instrument can also comprise at least one medication device or be embodied a as medication device. In this aspect, or else in other aspects, of the present invention, the medical consumable article can for example be a medicament or a therapeutic agent or comprise such a medicament or therapeutic agent or can for example be packaging of such a medicament or therapeutic agent or can be part of such packaging. The consumable article-specific information can for example comprise a dose, usage information, an expiry date or similar information.

In a further aspect of the present invention, a method is proposed for capturing an optical barcode connected to a moved carrier. In particular, this method can be carried out using a barcode reader and/or a device as per one or more of the above-described embodiments. Accordingly, reference can be made to the description above in respect of possible embodiments of the method. In the proposed method, information modules of the moved barcode are captured at least one-dimensionally. Furthermore, at least one clock track detector is used to capture clock track modules of a clock track of the barcode. Furthermore, at least one item of reference information from the barcode is captured by means of at least one reference detector. A movement direction of the carrier is deduced from at least one signal from the clock track detector and at least one signal from the reference detector.

In respect of further possible embodiments of the method, reference can be made to the description above. In particular, the reference detector can be configured to receive an optical signal which is selected from: an optical signal from the clock track at a predetermined spatial offset from the clock track detector, more particularly an offset parallel to the movement direction; an optical signal from a reference track which is separate from the clock track and has a module offset with respect to the clock track, i.e., for example, a reference track which is phase-shifted with respect to the clock track.

In conclusion, the following embodiments are envisioned within the scope of the present invention:

Embodiment 1

A barcode reader for capturing a barcode connected to a moved carrier, wherein the barcode reader comprises at least one optical barcode detector for at least one-dimensional capture of information modules of the barcode, wherein the barcode reader furthermore comprises at least one optical clock track detector for capturing clock track modules of a clock track of the barcode and at least one optical reference detector for capturing at least one item of reference information from the barcode, wherein the barcode reader is configured to deduce a movement direction of the carrier from at least one signal from the clock track detector and at least one signal from the reference detector.

Embodiment 2

The barcode reader according to the preceding embodiment, wherein the barcode reader is configured to capture at least one signal change caused by the clock track in the signal from the clock track detector, more particularly a positive or negative edge.

Embodiment 3

The barcode reader according to one of the preceding embodiments, wherein the barcode reader is configured to deduce the movement direction from a sign of a signal change captured by the clock track detector and an absolute value of the signal from the reference detector, more particularly a coincident signal from the reference detector.

Embodiment 4

The barcode reader according to the preceding embodiment, wherein the barcode reader is configured to deduce a first movement direction if a negative edge is identified in the signal from the clock track detector and a first signal level is identified in the signal from the reference detector or if a positive edge is identified in the signal from the clock track detector and a second signal level is identified in the signal from the reference detector; and to deduce a second movement direction in the opposite direction to the first movement direction if a positive edge is identified in the signal from the clock track detector and the first signal level is identified in the signal from the reference detector or if a negative edge is identified in the signal from the clock track detector and the second signal level is identified in the signal from the reference detector.

Embodiment 5

The barcode reader according to one of the preceding embodiments, furthermore comprising a data storage, wherein the barcode reader is configured to read out information contained in rows of the barcode and store it in the data storage, respectively with an address counter corresponding to the row, wherein the barcode reader is configured to increase or decrease the address counter incrementally in accordance with the identified movement direction.

Embodiment 6

The barcode reader according to one of the preceding embodiments, wherein the optical clock track detector is part of the barcode detector.

Embodiment 7

The barcode reader according to one of the preceding embodiments, wherein the reference detector is arranged with respect to the clock track detector in at least one of the following manners: the reference detector is arranged next to the clock track detector in a direction perpendicular to the movement direction; and the reference detector is arranged offset with respect to the clock track detector in a direction parallel to the movement direction by an offset, wherein the offset typically deviates from an even multiple of a module height of the modules of the barcode.

Embodiment 8

The barcode reader according to one of the preceding embodiments, comprising at least one optical sensor element, more particularly a sensor row, wherein the clock track detector and the reference detector are configured to use the optical sensor element.

Embodiment 9

The barcode reader according to one of the preceding embodiments, wherein the optical reference information is selected from: optical information from a reference track of the barcode; optical information from the clock track of the barcode at a predetermined offset from current optical information from the clock track read out by the clock track detector, more particularly at an offset deviating from an even multiple of a module height of the clock track.

Embodiment 10

The barcode reader according to one of the preceding embodiments, furthermore comprising a receptacle for receiving the carrier, wherein the receptacle is configured to enable movement of the carrier relative to the barcode reader, wherein the barcode reader is configured such that the barcode can be read out by means of the barcode reader while the carrier moves in the receptacle.

Embodiment 11

A device for transmitting at least one item of information, comprising at least one barcode reader according to one of the preceding embodiments, furthermore comprising at least one carrier with at least one barcode, wherein the barcode comprises a plurality of information modules and at least one clock track.

Embodiment 12

The device according to the preceding embodiment, wherein the clock track has a plurality of periodically alternating clock track modules, wherein the alternating clock track modules are configured to produce at least two different signal levels alternately in the clock track detector when passing the clock track detector.

Embodiment 13

The device according to one of the preceding embodiments relating to a device, wherein the clock track has a plurality of successive clock track modules, which are arranged successively along a straight or else curved line in the barcode and which do not simultaneously serve as information modules of the barcode but which only serve as a clock when the barcode is moved relative to the barcode reader.

Embodiment 14

The device according to one of the preceding embodiments relating to a device, wherein the barcode is a two-dimensional barcode.

Embodiment 15

The device according to one of the preceding embodiments relating to a device, wherein the barcode furthermore has at least one reference track.

Embodiment 16

The device according to the preceding embodiment, wherein the reference track is embodied as second clock track, wherein the reference track has the same periodicity as the clock track and has a phase shift compared to the clock track.

Embodiment 17

The device according to one of the two preceding embodiments, wherein the reference track is arranged parallel to the movement direction.

Embodiment 18

The device according to one of the three preceding embodiments, wherein the reference track has a plurality of periodically alternating reference track modules, wherein the alternating reference track modules are configured to produce at least two different signal levels alternately in the reference detector when passing the reference detector, wherein a periodicity of the reference track is phase-shifted compared to a periodicity of the clock track.

Embodiment 19

The device according to one of the four preceding embodiments, wherein the reference track has the same periodicity as the clock track.

Embodiment 20

The device according to one of the five preceding embodiments, wherein the reference track is aligned parallel to the clock track.

Embodiment 21

The device according to one of the preceding embodiments relating to a device, wherein modules of the barcode have a module height in the movement direction and a module width perpendicular to the movement direction, wherein the module height exceeds the module width, such as by at least a factor of 1.2, more typically by at least a factor of 1.5.

Embodiment 22

A barcode, comprising a plurality of information modules, wherein the barcode furthermore comprises a clock track for clocking a readout of the information modules by means of at least one barcode reader, wherein there is a relative movement between the barcode and the barcode reader in a movement direction, wherein the bar-code furthermore comprises at least one reference track which is embodied separately from the clock track, wherein the reference track has a phase offset compared to the clock track.

Embodiment 23

The use of a device according to one of the preceding embodiments relating to a device, for transmitting consumable article-specific information from at least one medical consumable article to a medical instrument interacting with the medical consumable article, more particularly to a medical measuring instrument and/or therapy instrument.

Embodiment 24

A method for capturing an optical barcode connected to a moved carrier, wherein information modules of the barcode are captured at least one-dimensionally, wherein at least one clock track detector is used to capture clock track modules of a clock track of the barcode, wherein furthermore at least one item of reference information from the barcode is captured by means of at least one reference detector, wherein a movement direction of the carrier is deduced from at least one signal from the clock track detector and at least one signal from the reference detector.

The above-described barcode reader, the device, the barcode, the use and the method render it possible to realize, in particular, a manually operated pull-type reader and/or swipe reader or longitudinal reader for two-dimensional barcodes, for which a constant pulling speed and also coordinated movement processes, in particular a unidirectionality of the readout of the data, are assumed. The presented solution renders it possible, in particular, to realize manually operated swipe, pull-type or push-type readers for both one-dimensional and two-dimensional barcodes, in which coordinated movement processes can largely be dispensed with. The invention can be applied particularly advantageously, but not exclusively, to goods in which one dimension is significantly larger than the other dimensions thereof, such as, for example, in the case of analytic test strips. However, the invention can also be applied to increase the reliability of differently realized barcode scanner systems.

For two-dimensional barcodes in particular, it is possible, according to the invention, to provide a cost-effective two-dimensional barcode reader system which can be implemented easily. In this case, the above-described optional features can be used alternatively or cumulatively. Thus, for example, a second, additional clock track can be used as reference track. The latter can interact with the actual clock track. By way of example, the geometry of the reference track can have an embodiment completely identical to the actual clock track, but can be arranged with a phase offset compared thereto.

If use is made of a clock track in which modules with a first signal level and modules with a second signal level alternate (binary clock track), it is possible, for example, for there to be a phase offset of half a module, which corresponds to a phase shift of 90° in the periodicity of the clock track. In this case, it is possible to realize, particularly by means of a discriminating coincidence method in which the signals from the clock track detector and the reference detector are compared, that each change in state in the two tracks, or at least some of the changes in state in these two tracks, is/are used both to determine a spatial resolution and to determine a movement direction. In principle, such methods are known from displacement encoder or rotation sensor technology from mechanical metrology. By contrast, the use of this principle, as proposed according to the invention, when decoding one-dimensional or else multidimensional barcodes, is not known. In the present case, this principle can, in particular, be used as partial algorithm in a barcode decoder algorithm.

Furthermore, there can be a change in the geometric arrangement of the optical scanner system and, in the further course, a removal of the introduced reference track, for example a direction track. Since two-dimensional barcodes according to the prior art often already comprise a clock track and in many cases are scanned at least by means of an optical row sensor with a plurality of light-sensitive elements (pixels), the additional reference track or direction track can, according to the invention, be dispensed with in one alternative provided that a second, additional sensor is arranged with spatial offset or phase offset in position space with respect to the clock track detector, for example with a phase offset of 90° over the already existing clock track. The barcode detector and/or the clock track detector and/or the reference detector or some or all of these detectors can optionally be embodied as so-called contact image sensors (CIS). This means that the detectors can rest practically directly on the barcode or can be arranged at a distance of at most 5 mm from the barcode. By way of example, such CIS sensors can be achieved in the form of a CCD row, optionally in combination with one or more deflection elements, for example with one or more split mirrors and/or prisms.

If use is made of conventional barcodes, in which there is a clock track but, however, no additional reference track such that the clock track itself is used twice—as actual clock track and as reference track—this additionally has the advantage of commercially avail-able camera scanners being able to be used and, according to the invention, it merely being an evaluation algorithm which needs to be adapted. In particular, this can occur if specific rules for designing the barcode must be adhered to, for example the use of so-called quiet zones, i.e. zones which do not contain any modules.

The above-described embodiment, in which use is made of a reference detector spatially offset compared to the clock detector, more particularly of a reference detector offset in the movement direction by a non-even multiple of half a module height, as a result of which the clock track can additionally be used as a reference track as well, has various further advantages. Thus, for example, use can be made of two-dimensional detectors, for example simple optical field sensors with a plurality of optical row sensors. Furthermore, use can be made of CCD cameras with a two-dimensional CCD array. In this case, use can for example be made of a row sensor or of part of this row sensor as clock detector, and another row or part of another row of the detector can be used as reference detector, for example a row with a phase distance of $(n \cdot 360°) + 90°$, i.e. a resultant phase spacing of 90° and/or, with respect to position space, for example with a phase spacing of $(n \cdot 2 \cdot H) + \frac{1}{2} H$. Depending on the width of the utilized barcode, more particularly of the two-dimensional barcode, only low demands are placed on the utilized optical field sensor in respect of the resolution thereof. By way of example, if the two-dimensional barcode (here for example the whole region) is distributed over the whole length, use can already be made of a simple mouse sensor, as is usually used in optical computer mice.

According to the embodiments of the invention, it is furthermore possible to stabilize against angle-offset errors. Since each pull-type and/or push-type reader generally comprises a guide of the consumable article to be scanned, it is necessary for this guide also to have sufficient headroom. However, this generally leads to an angle offset between the movement direction and the column directions or the direction of the clock track of the barcode relative to the movement direction. Errors when applying the barcode to the carrier, for example printing errors, can also bring about such an angle offset. As a result of changing the geometry of the barcode in such a way that the individual modules are elongated in the longitudinal direction, i.e. parallel to the intended movement direction, it is possible to achieve an adjustable stability against a certain value of the angle offset. The longer the modules are (greater module height), the greater the angle offset may be.

Furthermore, according to the invention, it is possible to realize a simple flat scanning system. In particular, this can be achieved by the use of contact image sensors (CIS), for example in the form of one or more CCD rows, the imaging of which can for example be realized in the region of 0.5 to 0.7 mm.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which:

FIGS. 12a and 12b show an exemplary embodiment of a barcode reader in the form of an optical contact reader, having an additional, phase-shifted sensor as reference detector;

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

As illustrated above, one idea of the present invention comprises reading out a barcode in such a way that two mutually phase-offset and sometimes coincident signals from a clock track detector and from a reference detector are compared. Here, these can either be signals which were recorded by means of the same clock track but with a spatial phase offset with respect to one another, or signals from a clock track and a separate, phase-shifted reference track of the barcode. Combinations of these options, or other embodiments by means of which the phase-offset signals can be produced, are also feasible.

Figure 1:
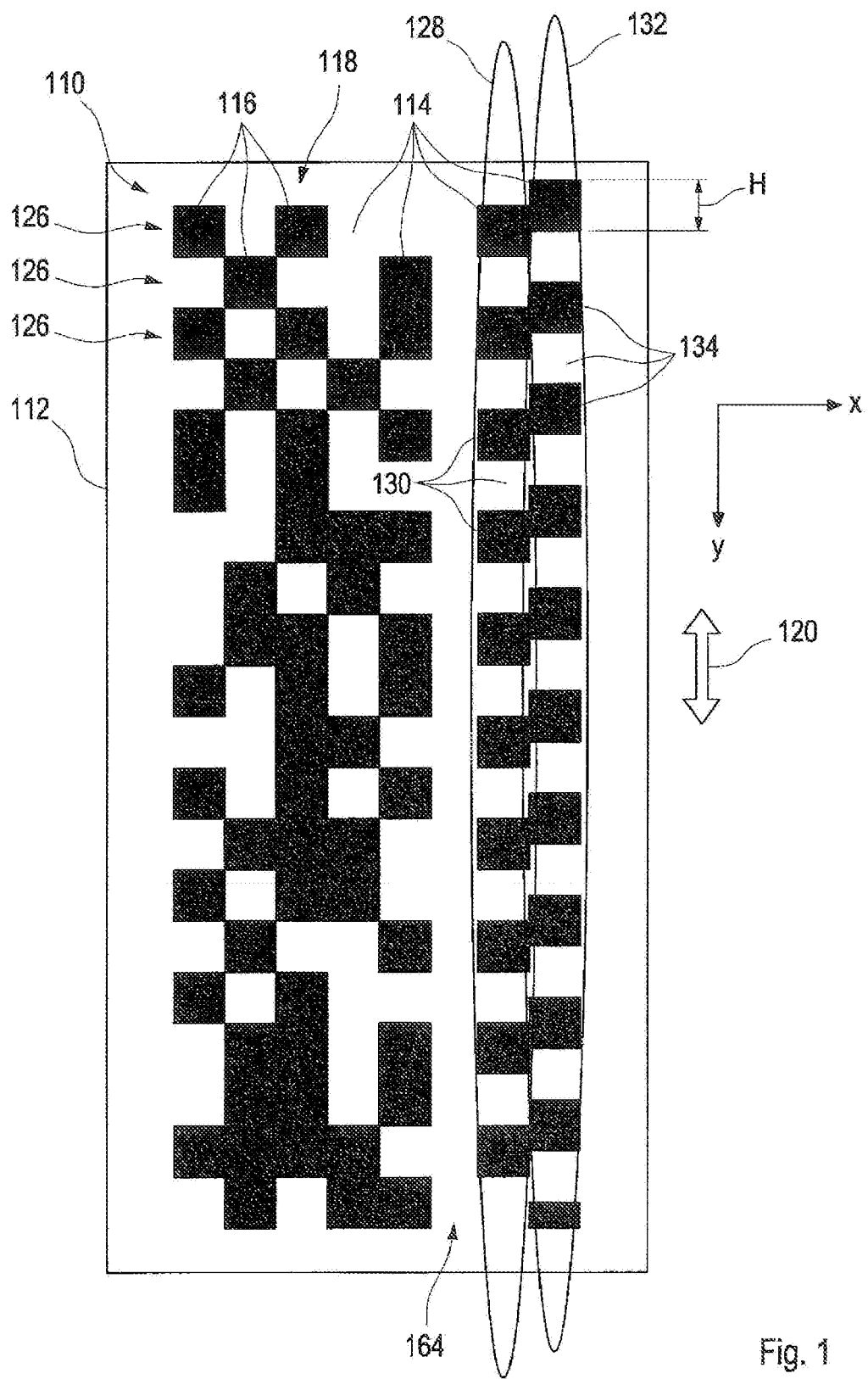
FIG. 1 shows a first exemplary embodiment of an enhancement according to the invention of a two-dimensional barcode with a clock track and a reference track embodied as direction track.
Figure 2:
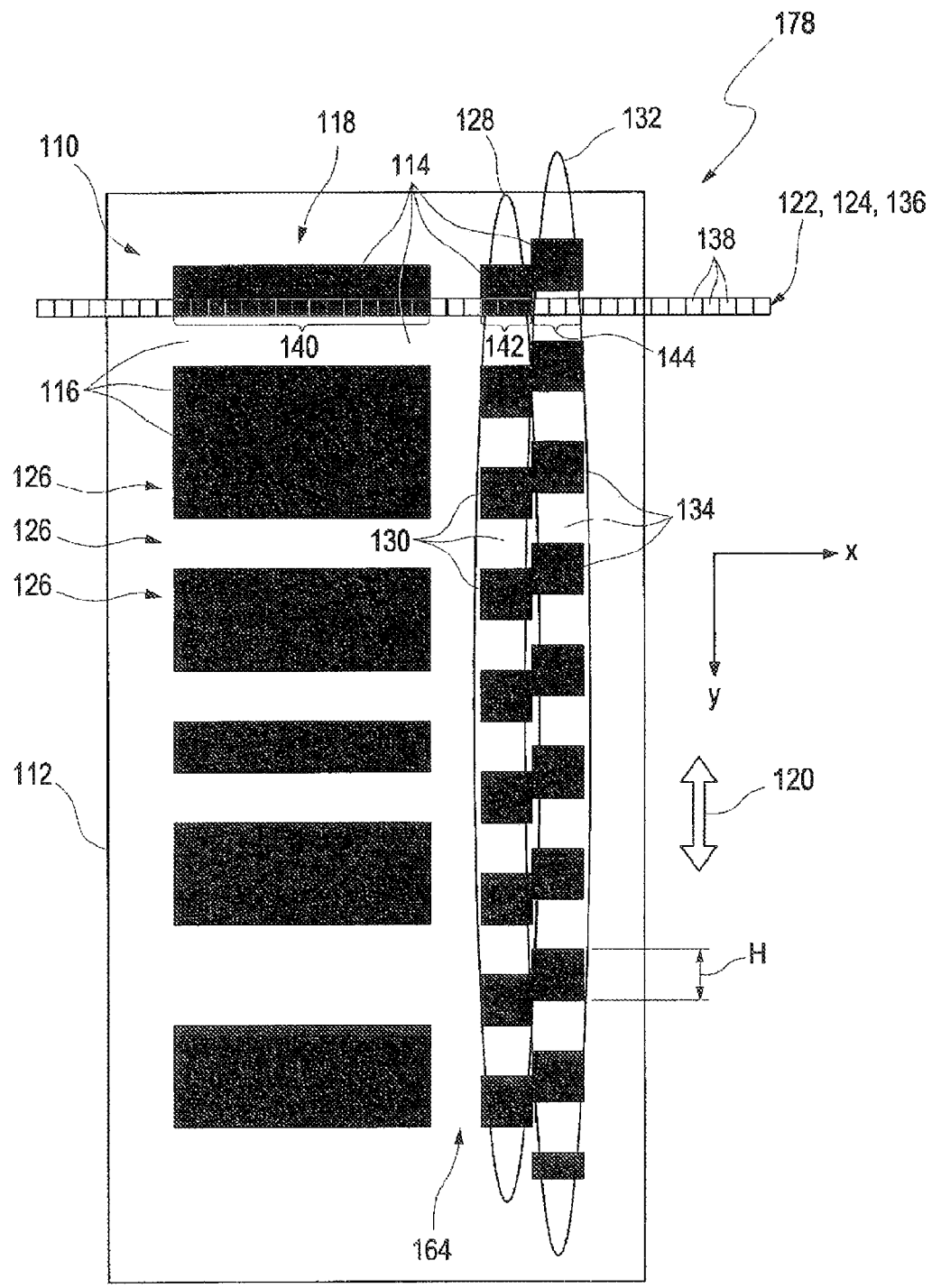
FIG. 2 shows a second exemplary embodiment of the enhancement according to the invention of a one-dimensional barcode with a clock track and a direction track in the form of an additional reference track.

FIGS. 1 and 2 illustrate, in an exemplary fashion, exemplary embodiments of two different embodiments of optical barcodes 110. By way of example, the barcodes 110 can each be applied to a carrier 112 or be connected to the carrier 112 in another way, for example be introduced into the latter. By way of example, the carrier can be a carrier of a test strip, for example of paper, a laminate, plastic or another material.

As information carriers, the barcodes 110 respectively have so-called modules 114. In principle, a module 114 is any region of the barcode 110, for example a predetermined rectangle, a square or, in the case of three-dimensional barcodes (which in principle are also possible), a predeterminable region in space, wherein these regions can each assume at least two optically measurable states. In the case of the illustrated, binary barcodes, in which the states for example relate to a reflectivity of a surface of the barcodes 110, these are the states "black", i.e. low reflectivity, and "white", i.e. high reflectivity. These two states can be assigned the numerical information "0" and "1" in arbitrary fashion.

The barcodes 110 respectively comprise a plurality of information modules 116, which are arranged in an information field 118 of the barcode 110. In the barcodes 110 illustrated in FIGS. 1 and 2, the information fields 118 are embodied as rectangular fields, with a width along an x-direction and a length along a y-direction, wherein the y-direction is ideally aligned parallel to a movement direction 120 of the carrier 112 relative to a detector 122 of a barcode reader 124, which is merely indicated in FIG. 2 and not illustrated in FIG. 1. The y-direction thus typically also constitutes an intended movement direction which however, as will be explained in more detail below, can also deviate from a true movement direction or actual movement direction.

While the one-dimensional barcode as per FIG. 2 merely has one information module 116 per y-coordinate, i.e. per row, the two-dimensional barcode as per FIG. 1 has a plurality of information modules 116 arranged next to one another for each y-coordinate in the information field 118, i.e. a plurality of information modules 116 per row 126. In the following text, modules 114 with the same y-coordinate are referred to as "row", and modules with the same x-coordinate are referred to as "column".

Furthermore, the barcode 110 in the exemplary embodiments as per FIGS. 1 and 2 respectively has a clock track 128. This clock track 128 is aligned parallel to the y-direction and typically has the same periodicity, i.e. the same repetition frequency of the modules 114, as the information modules 116 in the y-direction. Accordingly, the clock track 128 in the illustrated exemplary embodiments likewise comprises clock track modules 130, which in turn can assume at least two states. In the illustrated, binary exemplary embodiment, these once again are the states "black" and "white". In the illustrated exemplary embodiments, the clock track once again has a periodic embodiment in the y-direction, and so respectively periodic clock track modules 130 repeat with the same information, i.e. black and white clock track modules 130 alternate in this exemplary embodiment.

Here, the clock track 128 is typically not phase-shifted compared to the rows 126 of the information modules 116. This means that the clock track modules 130 respectively have the same y-coordinate as corresponding information modules 116 of a corresponding row 126.

Furthermore, the barcodes 110 as per the exemplary embodiments in FIGS. 1 and 2 optionally also have a reference track 132, which can also be referred to as direction track, because, for example, it is possible to determine a current direction of movement with the aid of the information contained in this reference track 132. The reference track 132 is in turn arranged parallel to the y-direction and in turn has reference track modules 134, which in turn can assume at least two states. In the illustrated, binary examples, these once again are precisely two states, namely a "black" and a "white" state. Here, the periodicity of the reference track modules 134 may in turn be identical to the periodicity of the information modules 116 and/or the clock track modules 130 in the y-direction, and the reference track modules 134 typically have the same module height (denoted by H in FIG. 1) in the y-direction as the clock track modules 130 and/or the information modules 116. However, the reference track 132 is phase-shifted compared to the clock track 128 and compared to the information modules 116. This means that, in terms of the y-coordinate thereof, the center of the reference track modules 134 deviates from the centers of the clock track modules 130, for example by half a module height H. By way of example, in the exemplary embodiment illustrated in FIGS. 1 and 2, the center of the black reference track modules 134 is respectively displaced by half a module height H in the direction of smaller y-coordinates. This will be explained in more detail below.

FIG. 2 symbolically illustrates a detector 122 as part of a barcode reader 124, relative to which the carrier 112 with the barcode 110 is moved. In the illustrated exemplary embodiment, the detector 122 as a whole is, in an exemplary fashion, embodied as a row detector 136 and can, for example, comprise an optical sensor row with individual optical sensors 138. However, in principle, other embodiments are also possible, for example by virtue of the detector 124 being embodied as two-dimensional detector with optical sensors 138 arranged in two dimensions, for example in the form of a detector which is usually used in a computer mouse. The optical sensors 138 can, for example, be embodied as CCD sensors, and so the row detector 136 can, for example, comprise a CCD sensor row. However, in principle, other embodiments are also possible.

In the illustrated exemplary embodiment, those optical sensors 138 of the row detector 136 past which the information modules 116 are guided when the carrier 112 moves in the movement direction 120 are referred to as barcode detector 140. Those optical sensors 138 which capture the clock track 128 when the carrier 112 moves are referred to as clock track detector 142 and those optical sensors 138 which capture the reference track 132 are referred to as reference detector 144. As shown in FIG. 2, these detectors 140, 142, 144 can, in an exemplary fashion, be embodied as separate detectors. However, as an alternative, it is also possible for two of these detectors to be embodied in combined fashion in such a way that, for example, as will be explained in more detail below, the clock track detector 142 is integrated into the barcode detector 140.

Figure 3:
FIGS. 3a to 3c show graphical representations of signal levels and changes in signal levels.
Figure 3:
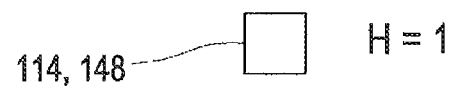
Figure 3:
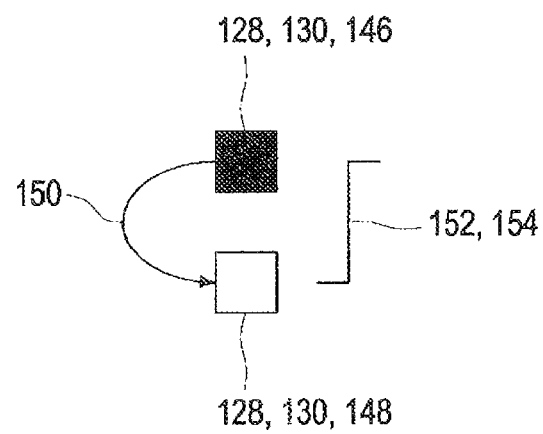
Figure 3:
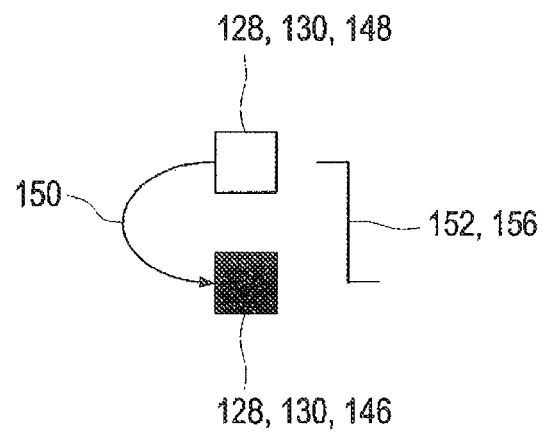

FIGS. 3a to 3c are used to explain different terminology used in the following text when discussing information storage and information reproduction in the barcode 110 and in the modules 114. As illustrated above, the barcode 110, in an exemplary fashion, is a binary barcode. Accordingly, there can, for example, be modules 114 which have low reflection and which are referred to as "low" modules 146 in FIGS. 3a to 3c, and also modules 114 which have high reflectivity and are accordingly referred to as "high" modules 148 in FIGS. 3a to 3c. By way of example, the low modules 146 can be interpreted as "zero" and the high modules 148 can be interpreted as "one". This is illustrated in an exemplary fashion in FIG. 3a.

FIGS. 3b and 3c illustrate the signal from the clock track detector 142 in the case of a transition from a low module 146 to a high module 148 (FIG. 3b) and in the case of a transition from a high module 148 to a low module (FIG. 3c). Here, the change in state is denoted symbolically in FIGS. 3a and 3b by reference sign 150. Such a change in state necessarily occurs in the case of movement of the carrier 112 in the movement direction 120 when the clock track detector 142 passes a transition between two modules 130 in the clock track 128. In this exemplary embodiment, the clock track detector 142, like the other detectors 140, 144 as well, detects reflected light from the barcode 110. However, as explained above, it is in principle possible for other optical signals to be detected as well. In accordance with the change in state 150, there is a change in the intensity of the reflected light during the transition, which results in a transition edge 152 in the signal from the clock track detector 142. This transition edge is embodied as positive edge 154 in the case of the transition as per FIG. 3b and as negative edge 156 in the case of the transition as per FIG. 3c.

Figure 4:
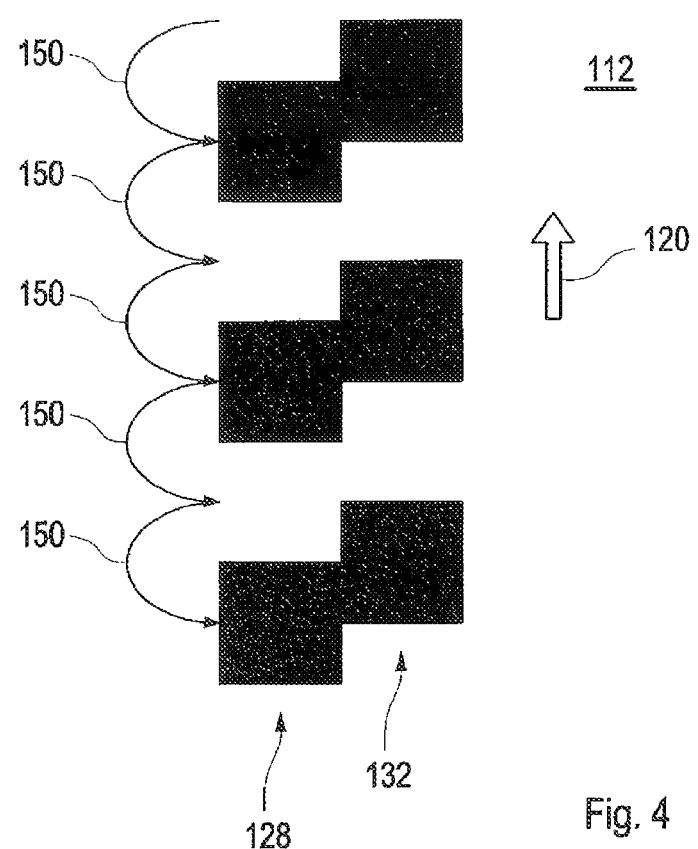
FIG. 4 shows a change in state in a clock track and a reference track with respect to the clock track.

FIG. 4 illustrates a sequence of changes in state 150 in the case of a movement of the carrier 112 relative to the row detector 136 (not illustrated in FIG. 4) in respect of the clock track 128. Here a change in state 150 respectively is a transition from a low module 146 to a high module 148, or vice versa.

FIGS. 5a to 5d explain an exemplary embodiment of a method according the invention as to how the signals from the clock track detector 142 and from the reference detector 144 render it possible to deduce the movement direction 120, i.e. the sign of the movement of the carrier 112 relative to the barcode reader 124 and there, more particularly, relative to the detector 122, for example relative to the row detector 136. The object of the method is to read out information from the rows 126 of the barcode 110, more particularly of the information field 118, in succession and to assign this to correct addresses, i.e. storage spaces with correct row-counter address, in a data storage such that, for example, the content of the information field 118 can subsequently be stored correctly as function of a row counter in a data storage. Here, the row counter for example specifies the absolute coordinate of the row 126 on the y-axis or a counter equivalent to this value. However, in principle, other embodiments are also possible.

The signal from the clock track detector 142 is respectively illustrated on the left-hand side in FIGS. 5a to 5d. Here, as an example, it is not the absolute value of this signal that is evaluated by the shown algorithm, but rather a change in this signal, symbolized here by a transition edge 152. Next to this, a state of the reference track 132 is respectively presented with a capital letter "L" or "H", which state is denoted by reference sign 158 in FIGS. 5a to 5d. In particular, this can be an absolute value of a signal from the reference detector 144 or a signal derived therefrom. In this case, it is coincident signals from the reference detector 144 and from the clock track detector 142 which are considered in particular, i.e. signals which occur substantially simultaneously within the meaning of the definition above.

Figure 5:
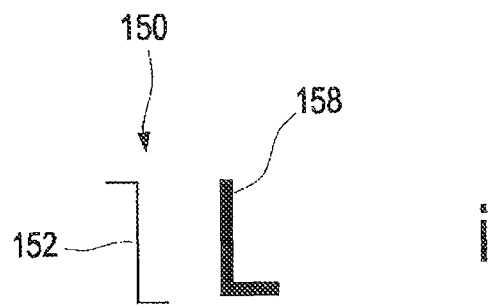
FIGS. 5a to 5d show various coincidences of signals in the clock track and in the reference track and the conversion thereof into an incremental increase or decrease of an address counter.
Figure 5:
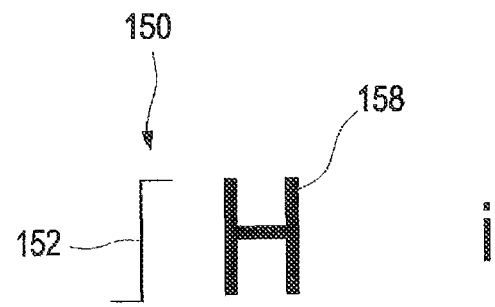
Figure 5:
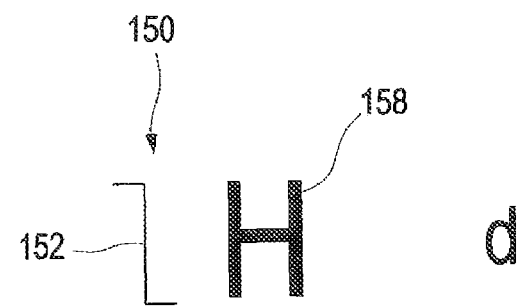
Figure 5:
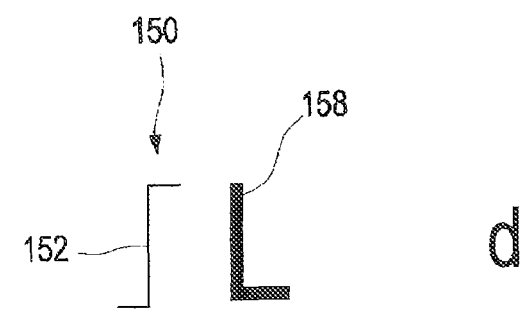

Here, as per FIGS. 5a to 5d, different coincident signals can occur in the process. If there is a change in state 150 on the clock track 128, i.e. if the clock track detector 142 passes a boundary between two clock track modules 130, the following coincidences can occur:

FIG. 5a: transition from high to low (i.e. negative edge) and low or zero state of the reference track 132. This means, as can easily be explained on the basis of FIG. 1, that, in the illustrated exemplary embodiment as per FIGS. 1 and 2, in which the reference track modules 134 are displaced upward compared to the clock track modules 130, for example by a value which is no more than one module height, such as exactly half a module height H, the carrier 112 moves upward relative to the detector 122. In this respect, the address of the data storage at which the informative part of the barcode 110 is stored, i.e. the content of the information modules 116 of the row associated with the respective clock track module 130, i.e. the row counter, can be increased incrementally and the informative part of the barcode 110 of the associated row can thereupon be written into this storage. Here, the incremental increase is respectively denoted by a small i in FIGS. 5a to 5d, and an incremental decrease of the row counter is denoted by d.

FIG. 5b: transition from low to high (i.e. a positive edge) and the state of the reference track 132 is high or one. In this case, the row counter can be increased incrementally (i), and the informative part of the barcode 110 can thereupon be written into the storage.

FIG. 5c: transition from high to low (i.e. a negative edge) and the state of the reference track 132 is high or one. In this case, the row counter can be decreased incrementally (d), and the informative part of the barcode 110 can thereupon be written into the storage.

FIG. 5d: transition from low to high (i.e. a positive edge) and the state of the reference track 132 is low or zero. In this case, the row counter can be decreased incrementally (d), and the informative part of the barcode 110 can thereupon be written into the storage.

Figure 6:
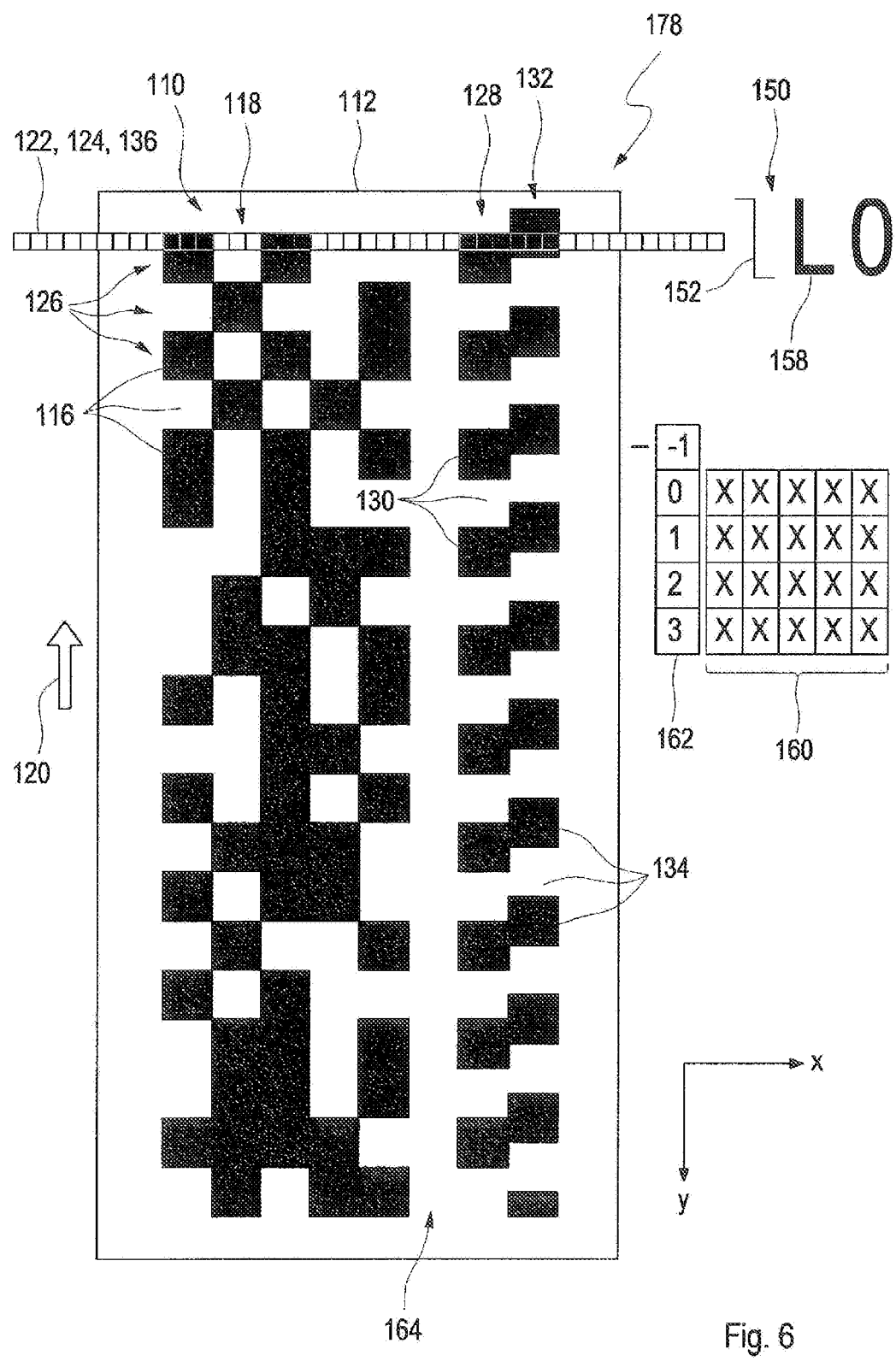
FIG. 6 shows a schematic illustration of reading information from a two-dimensional barcode.

This functional principle should be explained once again on the basis of an exemplary illustration in FIG. 6. A carrier 112 is once again illustrated here, to which a barcode 110 has been attached which is, in an exemplary fashion, embodied analogously to FIG. 1. Here, the carrier 112 is displaced relative to the detector 122 of the barcode reader 124 in a movement direction 120, which can also be referred to as the advance direction. A data storage 160 is also illustrated, in which the information contained in the information modules 116 of the information field 118 of the barcode 110, which is read out by means of the detector 122, should be stored, to be precise at an address 162 which corresponds to the respective row 126 and which can therefore also be referred to as row counter. Accordingly, the data storage 160 has five storage spaces for each value of the address 162 in the illustrated exemplary embodiment because five information modules 116 are provided in an exemplary fashion in each row 126 in the illustrated exemplary embodiment. In an exemplary fashion, the address 162 in the exemplary embodiment as per FIG. 6 starts with an initial value −1. However, it is self-evident that other embodiments are also possible.

By way of example, the barcode 110 on the carrier 112 can be read out by means of a row detector 136. Other embodiments are also possible, wherein reference can be made to the description above. The clock track 128 ensures the necessary changes in state 150, which are represented by the symbol of the transition edge 152. The state 158 of the reference track 132, read after or coincidentally with a change in state in the clock track 128, is likewise illustrated in FIG. 6, just as the state of the address 162 of the data storage 160, into which the informative part of the barcode 110 is read.

Figure 7A:
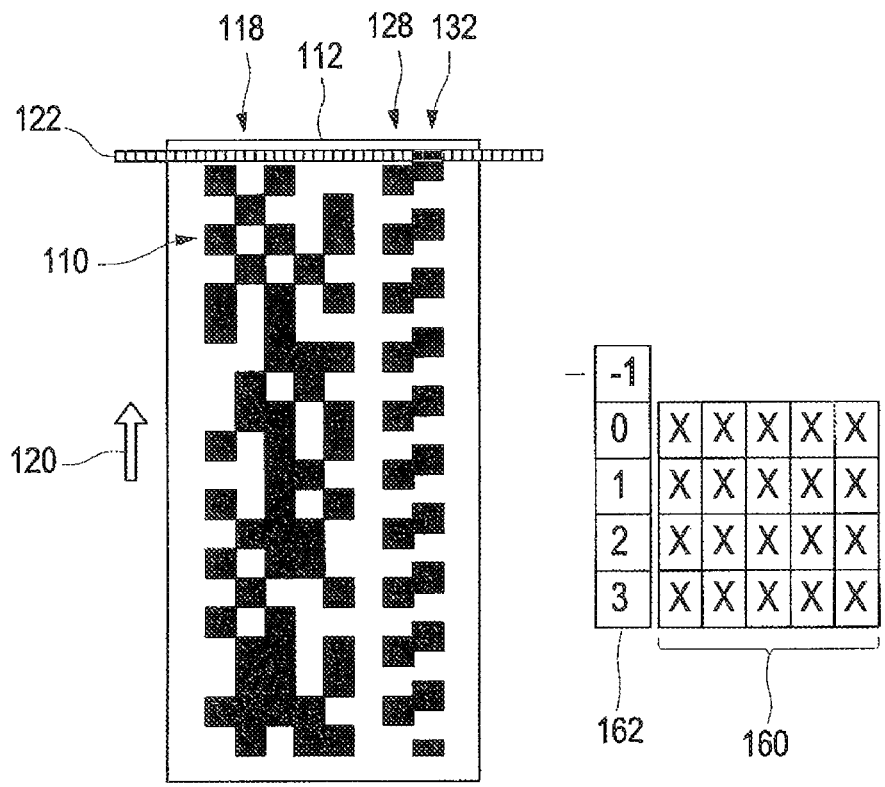
FIGS. 7a to 7o show a sequence of changes in state in a two-dimensional barcode during the reading process and the corresponding transmission of information into a data storage.
Figure 7B:
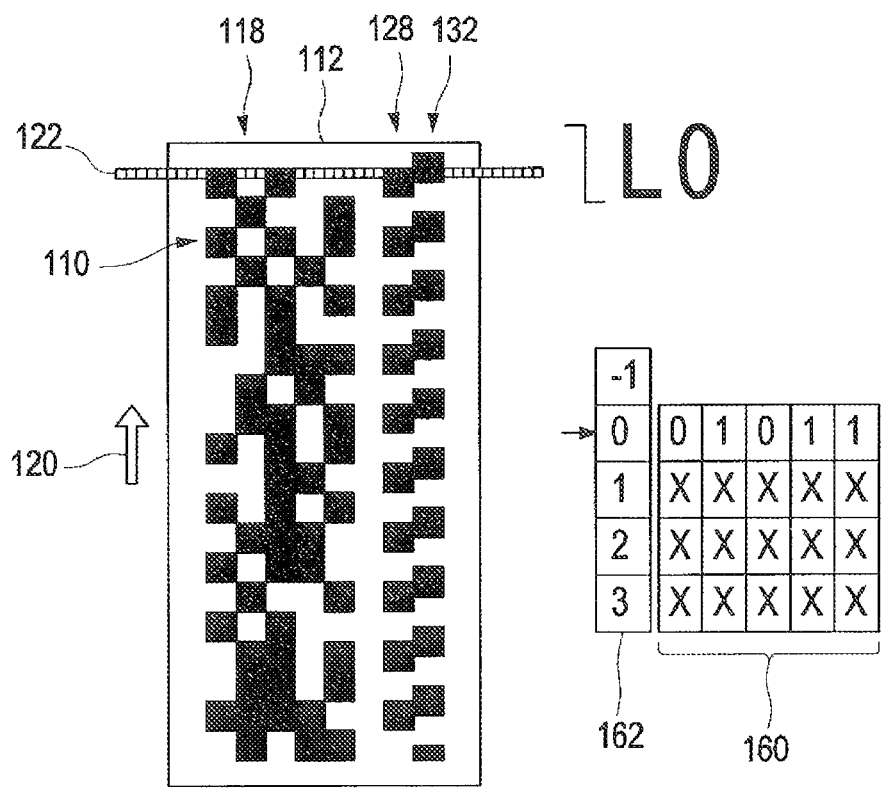
Figure 7:
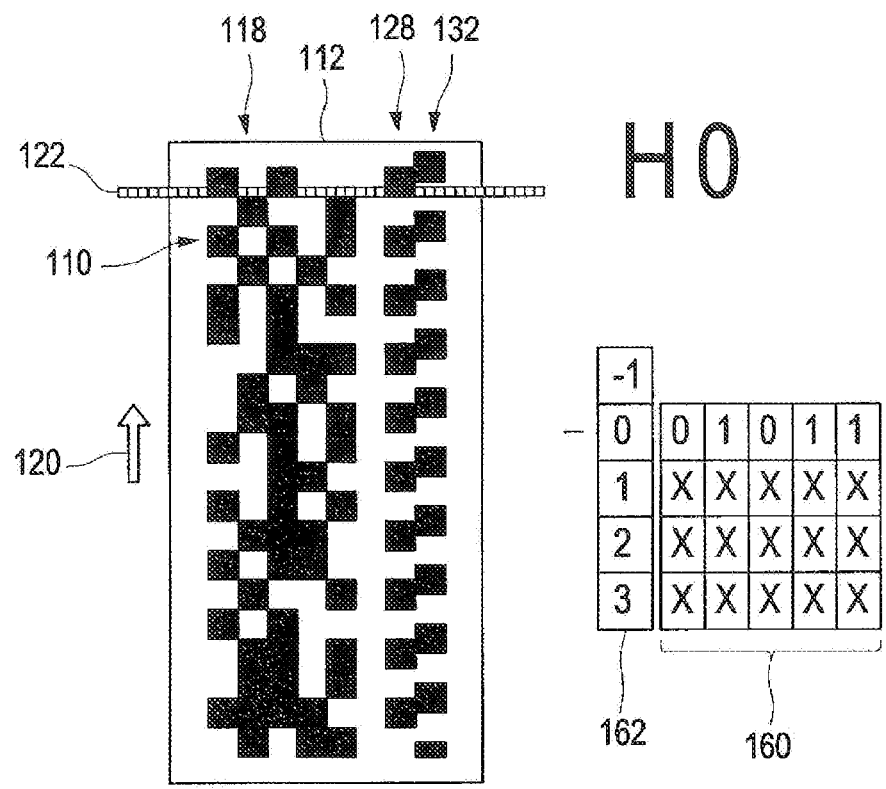
Figure 7:
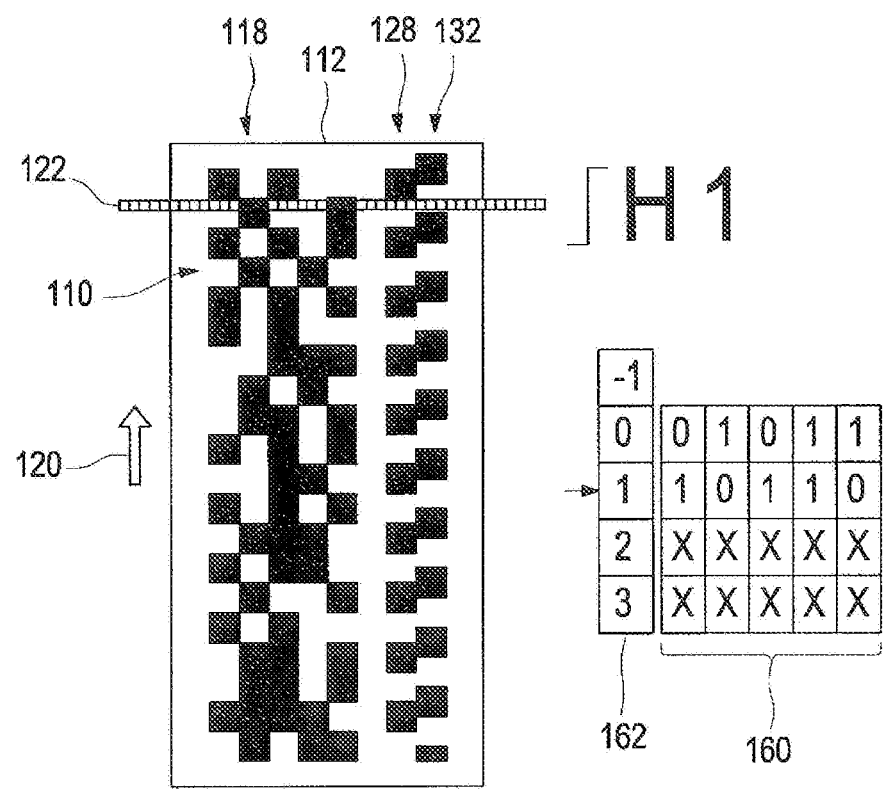
Figure 7:
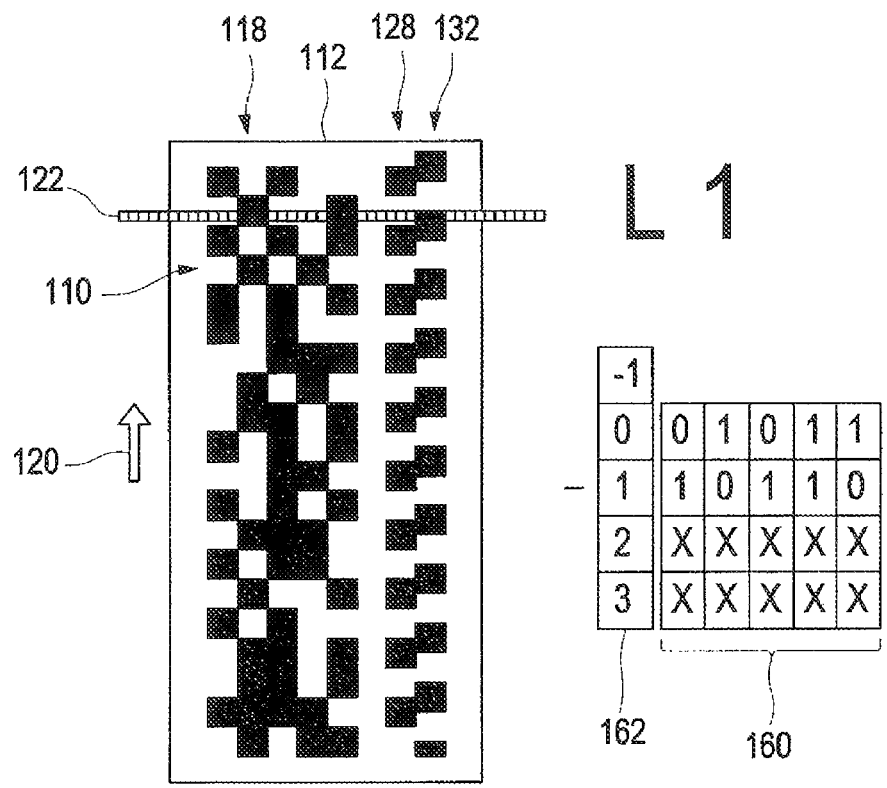
Figure 7:
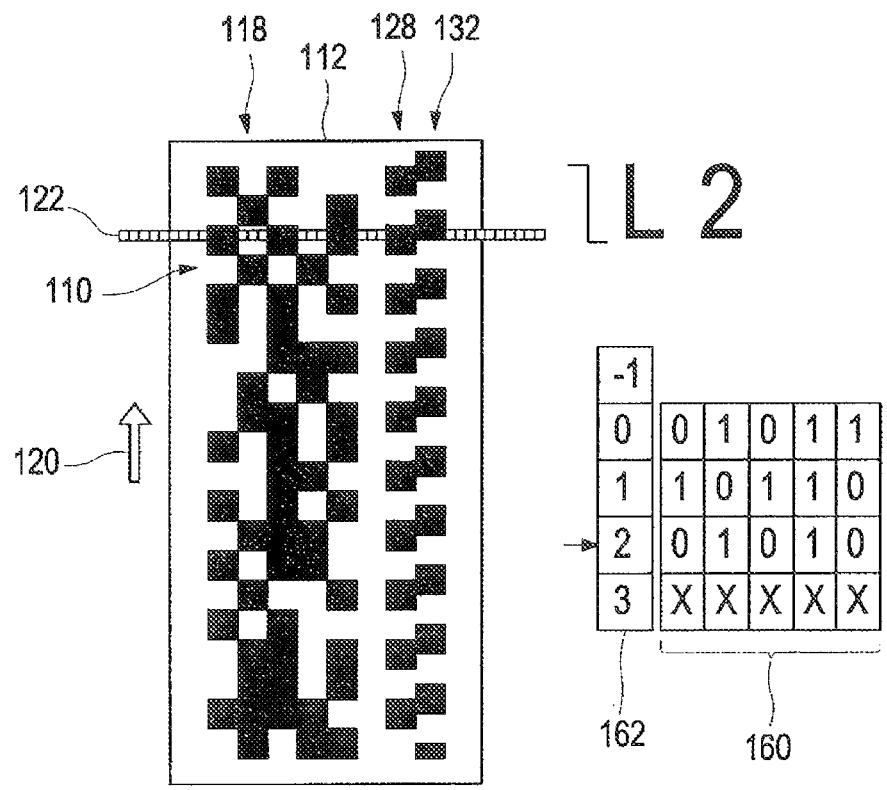
Figure 7:
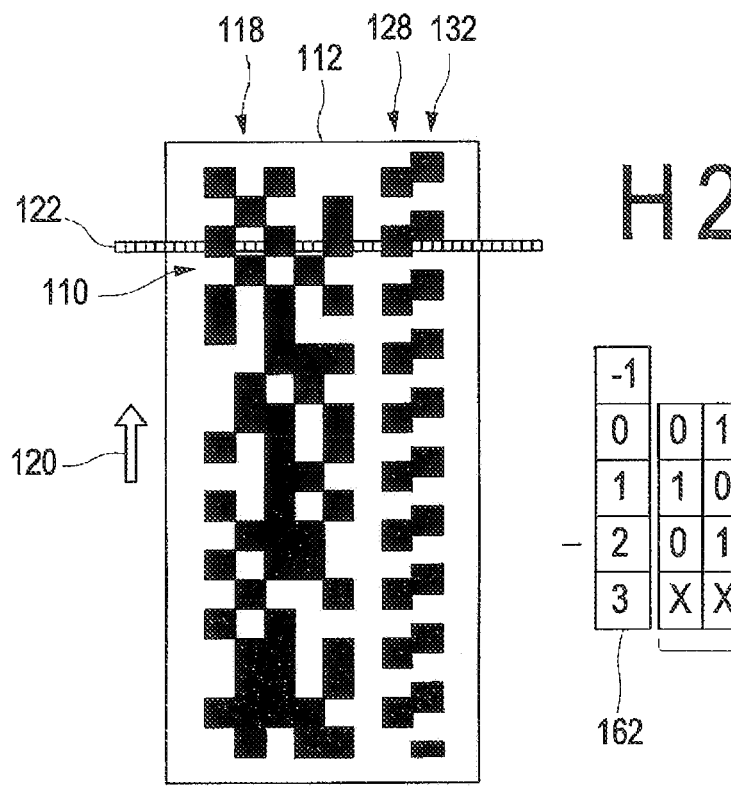
Figure 7:
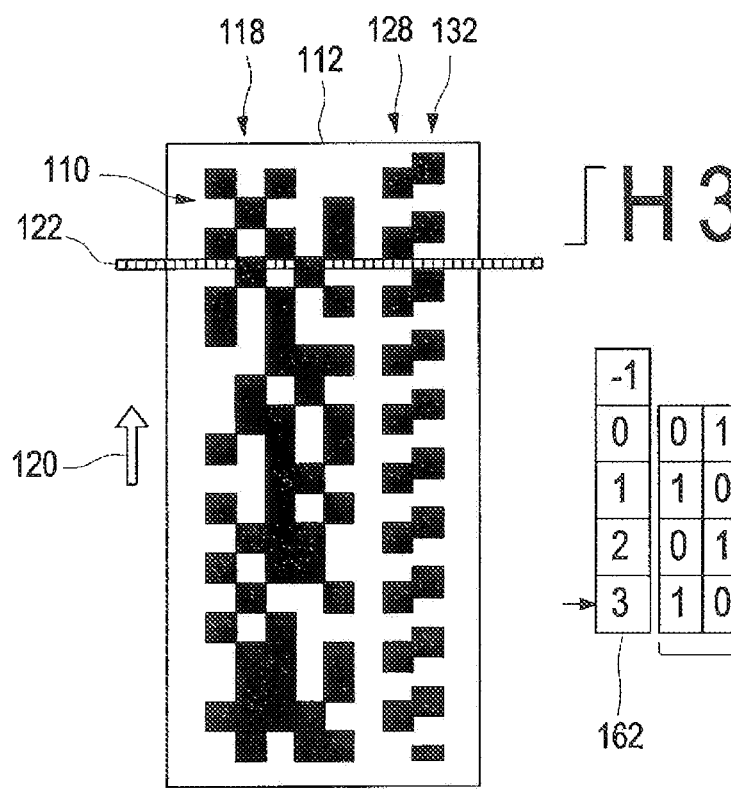
Figure 7:
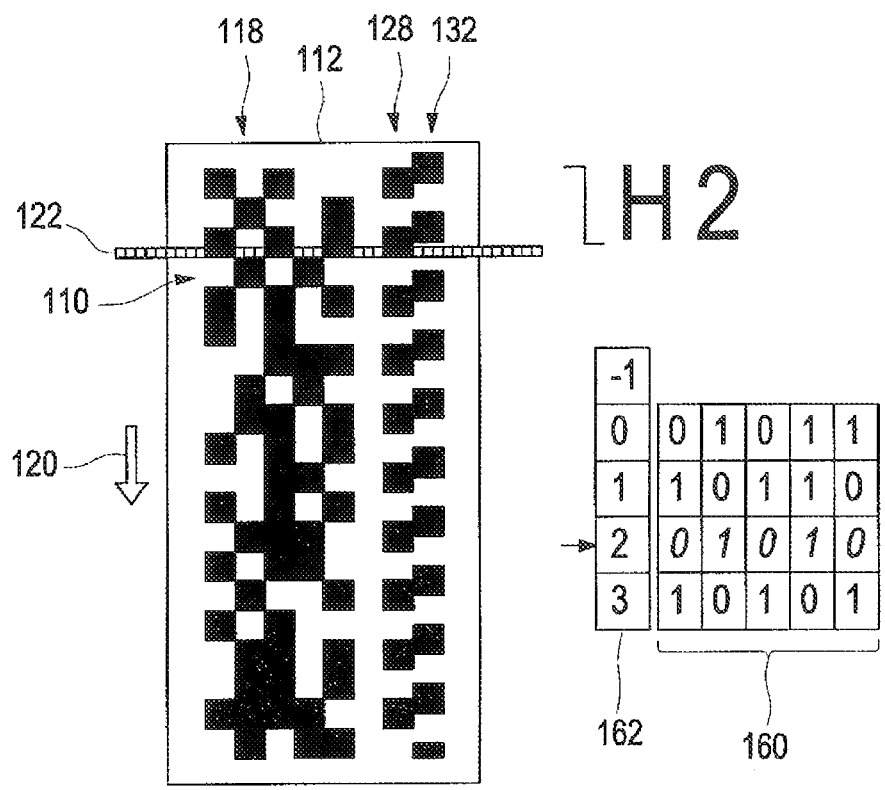
Figure 7:
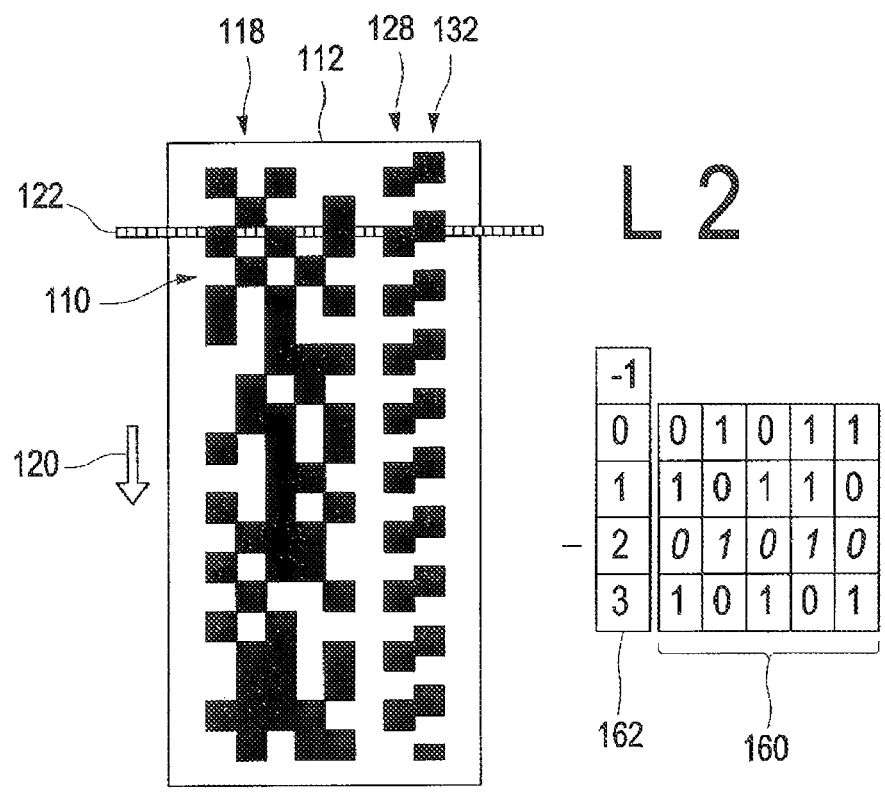
Figure 7:
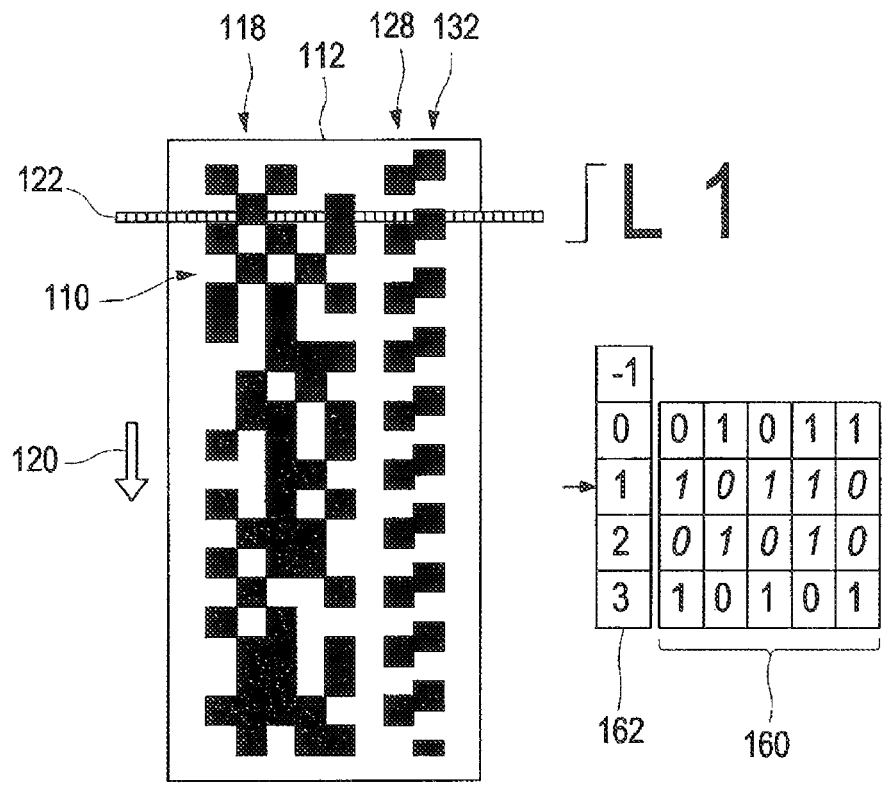
Figure 7:
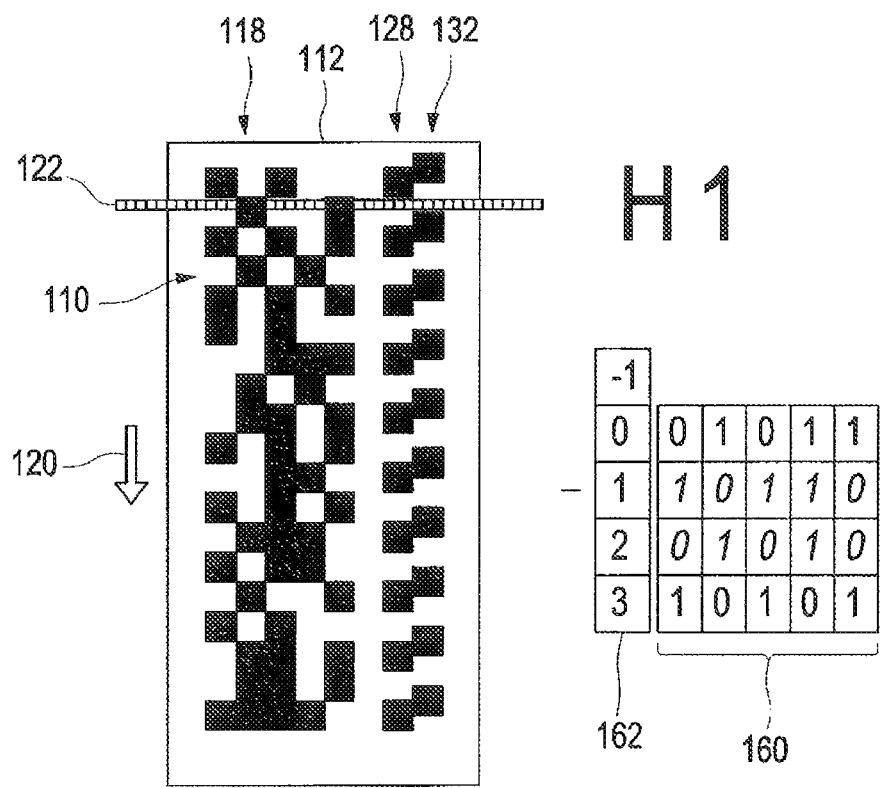
Figure 7:
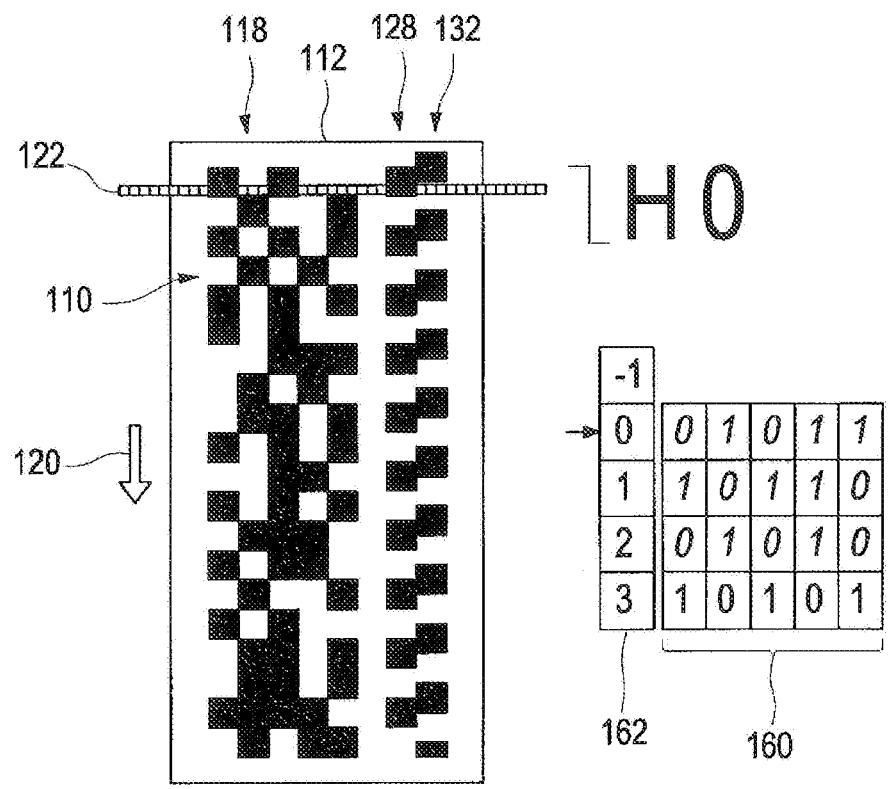
Figure 7:
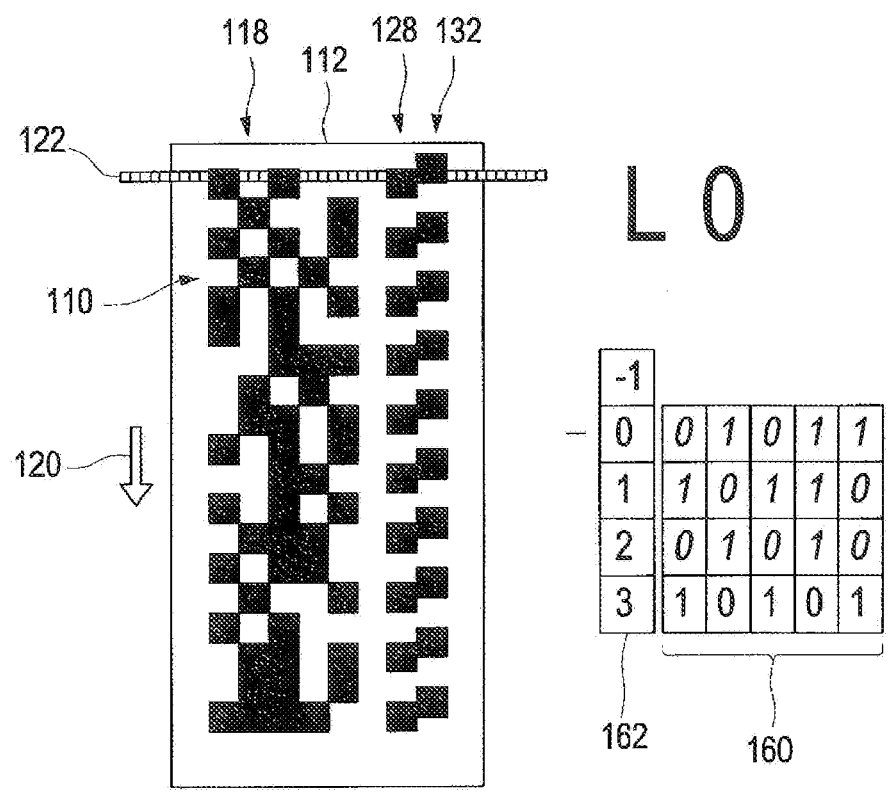
Figure 7:
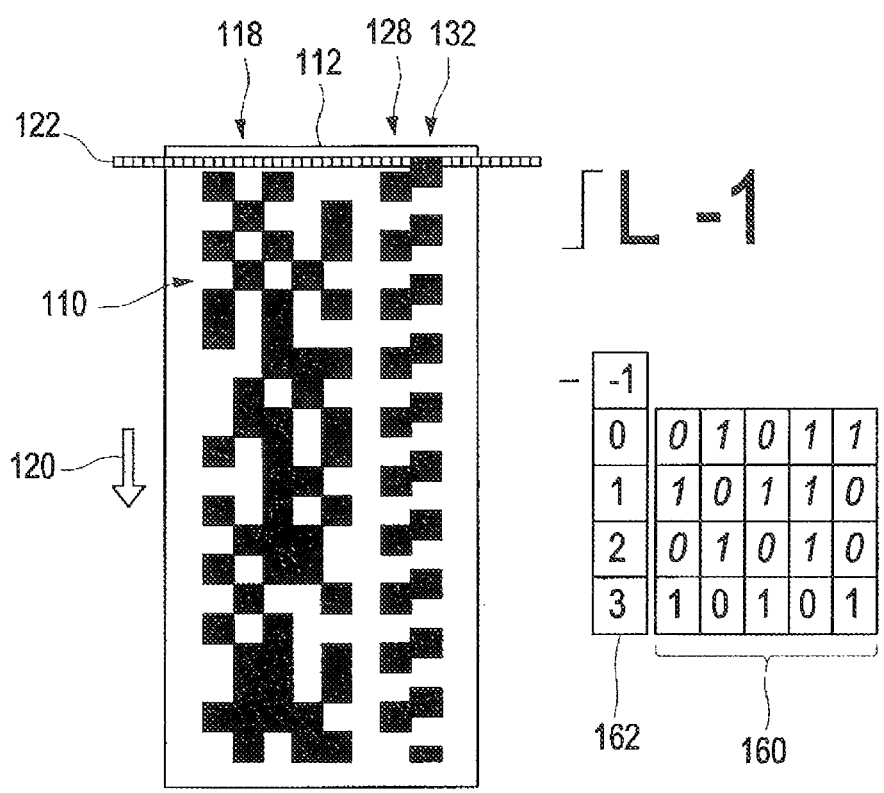

A sequence of changes in state in FIGS. 7a to 7o is used to describe the sequence of a read-in program. Here, in FIGS. 7a to 7h, the carrier 112 of the barcode 110 is transported upward in the Figures, relative to the detector 122. By contrast, in FIGS. 7i to 7o the carrier 112 is transported downward, i.e. there was a directional change between FIGS. 7h and 7i.

By way of example, the starting point is a preset (preset value) of the address 162, i.e. of the row counter, to a value of −1, as illustrated in FIG. 7a. A negative edge is reached in FIG. 7b, with a simultaneous low value of the reference track 132, as a result of which the row counter 162 is increased by 1 to a value of 0, and the corresponding information of the current row is read into the row of the data storage 160 associated with this value 0. In FIG. 7c, the carrier 112 moves on, without a change in state occurring. A new change in state is reached in FIG. 7d; in this case a positive edge in the signal from the clock track detector 142, accompanied by a high value of the signal from the reference detector 144. Once again, the row counter is correspondingly increased incrementally to the value 1 and the information from the barcode detector 140, subsequently read until another change in state, is stored in the row of the data storage 160 associated with this value 1. FIG. 7e illustrates a state in which, once again, there is no change in state 150 in the signal from the clock track detector 142. Then, in FIG. 7f, there is a negative edge, accompanied by a low state, which in turn leads to an incremental increase and reading of a corresponding row. In FIG. 7g there is no further change in state. In FIG. 7h, a positive edge occurs once again, accompanied by a "high" state of the reference detector 144, which in turn leads to an incremental increase of the row counter 162 and the information from the barcode detector 140 being read into the corresponding row of the data storage 160.

As explained above, a negative edge in the signal from the clock track detector 142 suddenly occurs once again between FIGS. 7h and 7i in the illustrated exemplary embodiment of a sequence, accompanied by a high (H) state in the signal from the reference detector 144. As explained above, this leads to the identification of a directional change, i.e. a reversal in the advance or movement direction 120. Accordingly, the row counter 162 is incrementally decreased rather than continuing to be incrementally increased. The information then read from the barcode detector 140 can either be discarded or can lead to a correctness treatment of the already read row in the data storage 160 (represented by italics in FIG. 7i). This is how testing can take place. No change in state in the signal from the clock track detector 142 is once again recorded in FIG. 7j, and so the address 162 of the row counter remains unchanged. In FIG. 7k, a positive edge occurs once again, accompanied by a low value, leading to a further incremental decrease in the row counter 162, wherein the information content from the barcode detector 140, read in the process or thereafter, up until the next change in state 150, can once again be used to check the already stored data of this row in the data storage 160. There once again is no change in state in FIG. 7l. In FIG. 7m, a negative edge occurs once again, accompanied by a high value, leading to a further incremental decrease in the row counter 162. There is no further change in state in FIG. 7n and there once again is a positive edge, accompanied by a low value, in FIG. 7o, leading to a further incremental decrease of the address 162 to the pre-set value −1. When the preset value in the row counter 162 is reached once again, it is therefore possible to deduce that, for example, the start of the barcode 110 has been reached.

In the exemplary embodiments as per FIGS. 1 and 2, the information field 118 and the clock track 128 and/or the reference track 132 are separated from one another in an exemplary fashion by a quiet zone 164. Here, a quiet zone 164 is generally understood to mean a spacing such that the clock track 128 and/or the reference track 132 do not directly adjoin the information modules 116 in the information field 118. However, this is not necessarily the case, and so the clock track 128 and/or the reference track 132 can also be wholly or partly integrated into the information field 118. However, the clock track 128 and, optionally, the reference track 132 as well should still have clock track modules 130 and, optionally, reference track modules 134 in the movement direction 120, which modules have alternating information content, for example alternating black and white modules or low and high modules, typically with the same periodicity as the information modules 116 of the information field 118.

A clock track 128 is already contained in some conventional two-dimensional barcodes, even if one or more additional reference tracks 132, which may be aligned parallel to the clock track 128, have not been disclosed previously. FIGS. 8 to 11 show various exemplary embodiments of barcodes 110, in which a clock track 128 is integrated in an information field 118 of the barcode 110. This can be illustrated in an exemplary fashion using the example of so-called "data matrix" barcodes.

Figure 8:
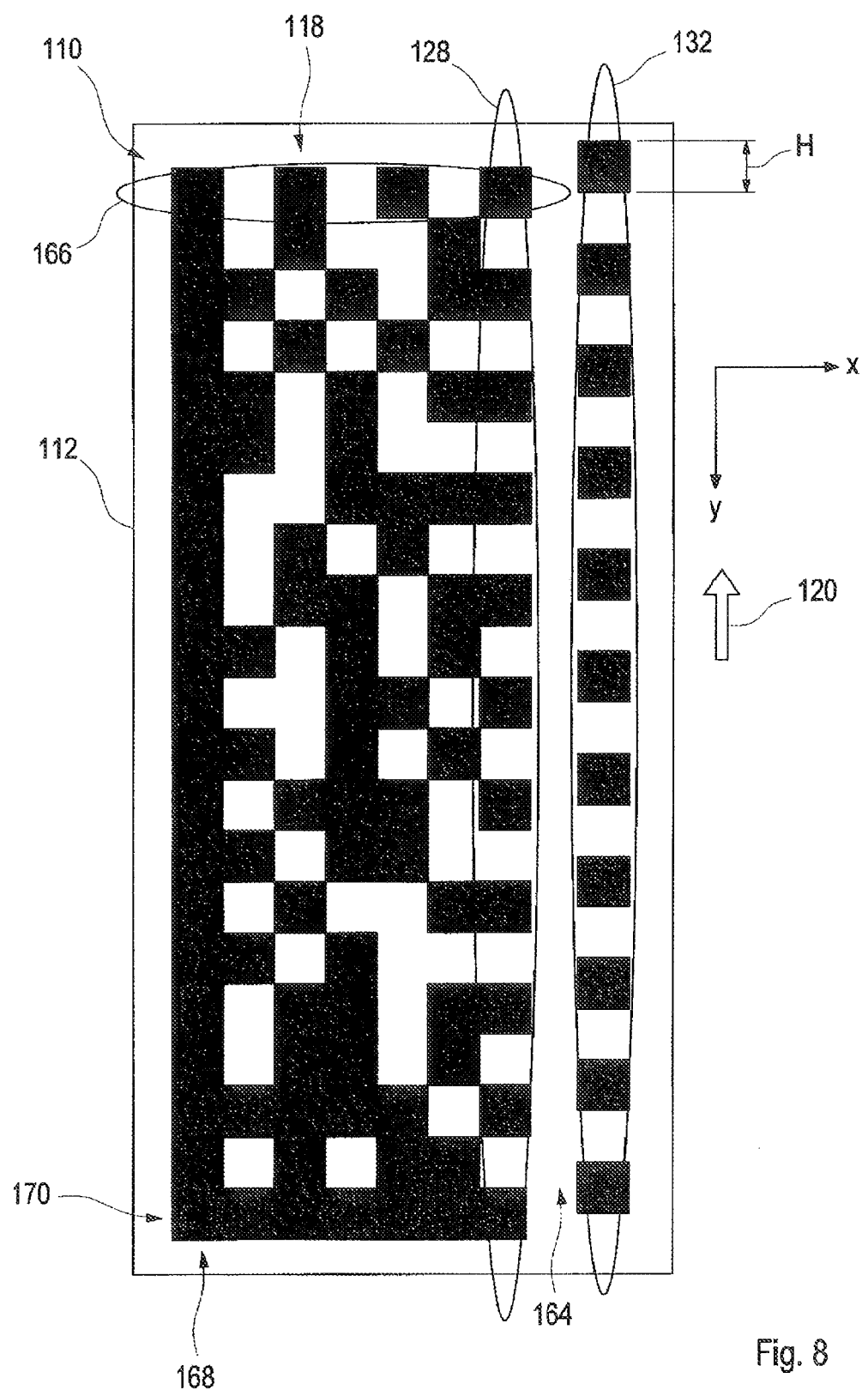
FIG. 8 shows a two-dimensional data matrix code, which already contains a clock track but to which an additional reference track was added.

Thus, FIG. 8 shows an exemplary embodiment in which a clock track 128 is already contained in the information field 118 as outermost column, having the same properties as the clock track 128 in, for example, the exemplary embodiment as per FIG. 1. Furthermore, although this should not be considered in any more detail within the scope of the present invention, there optionally is an additional clock track 166 in the x-direction. Furthermore, the outermost column is optionally completely filled with low values in the y-direction on the longitudinal side lying opposite to the clock track 128 such that a longitudinal bar 168 is created. Analogously, the last row of the information field 118 can be completely filled with low values at the end of the information field 118 lying opposite to the additional clock track 166 such that a transverse bar 170 is created. The longitudinal bar 168 and the transverse bar 170 together form an "L". The quiet zone 164 and the L or parts of the L, for example merely the longitudinal bar 168 or the transverse bar 170, can be used for black/white balancing and/or for positioning a detector 122.

Merely the reference track 132 is added to this information field 118 in the exemplary embodiment as per FIG. 8. By way of example, this reference track is, in principle, embodied as shown in the exemplary embodiment as per FIG. 1 and typically has the same periodicity in the y-direction as the modules of the clock track 128; however, it is phase-shifted compared to this clock track 128, for example by a non-even multiple of half of the module height H. By way of example, this can in turn be a phase shift by half a module height H or by an odd multiple of half a module height. The reference track 132 acting as direction track, which extends in the y-direction, i.e. parallel to the optimal movement direction 120, has in turn been added to the barcode 110 in this exemplary embodiment in such a way that the quiet zone 164 between the information field 118 with the clock track 128 and the reference track 132 is maintained. Inter alia, this offers the advantage of the illustrated barcode 110 still being able to be read by commercial readers, optionally even without use of the proposed method.

Figure 9:
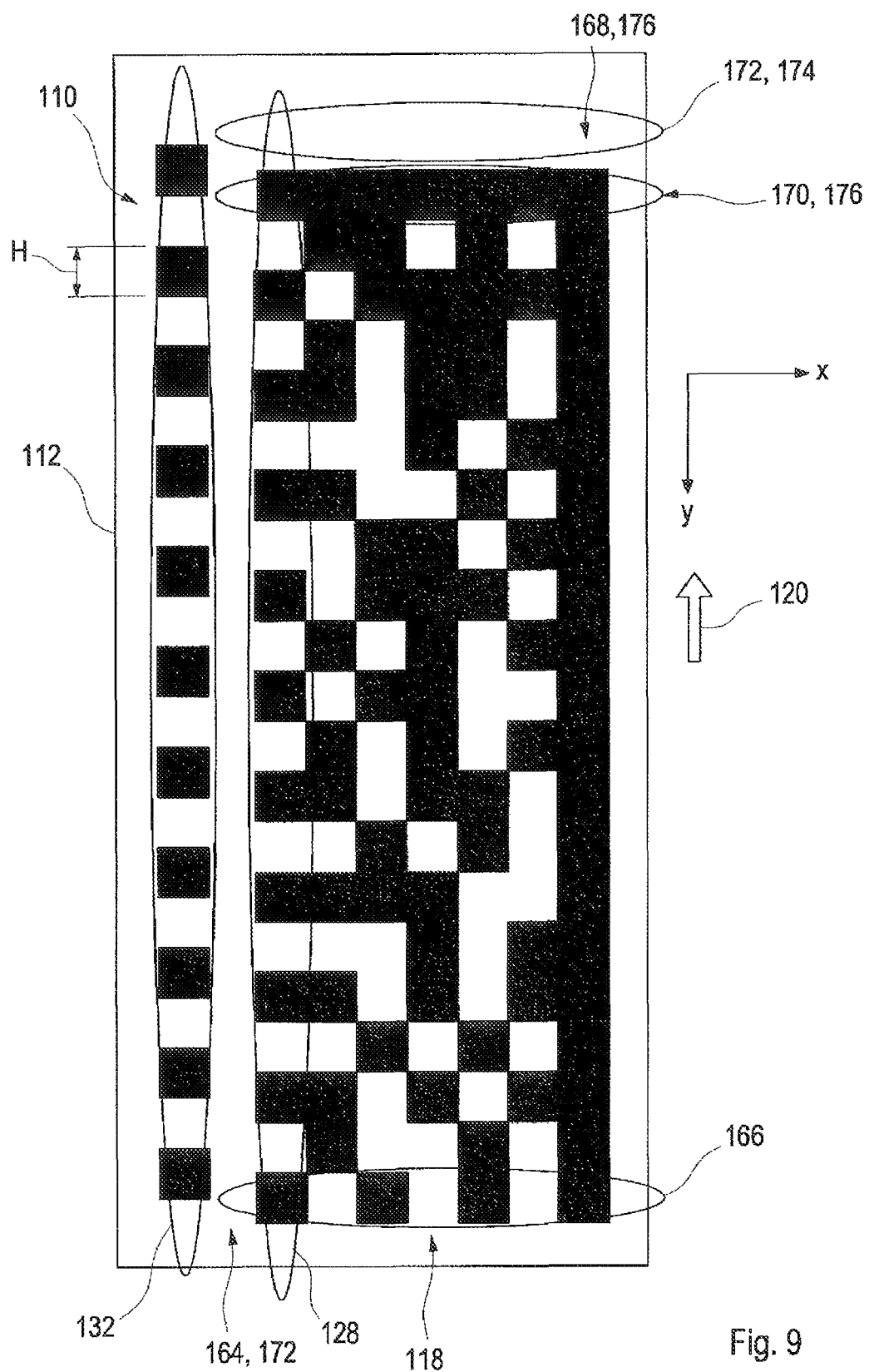
FIG. 9 shows a barcode rotated by 180° compared to the embodiment in FIG. 8, in which a quiet zone and an L-finder of the barcode can be used as white-value reference and black-value reference.

FIG. 9 illustrates an exemplary embodiment in which the two-dimensional barcode 110 in principle corresponds to the barcode 110 as per FIG. 8, whereas, however, the carrier 112 with the barcode 110 is rotated by 180° compared to the exemplary embodiment in FIG. 8. The advance direction, i.e. the movement direction 120, by contrast remains the same. This means that the barcode 110 is read in the reverse sequence. In this case, the quiet zone 164 in particular can be used as white-value reference 172. As an alternative or in addition thereto, it is possible to use a further quiet zone 174 above the transverse bar 170 as a white-value reference 172. The transverse bar 170 itself can be used as black-value reference 176. As an alternative or in addition thereto, the longitudinal bar 168 can also be used as black-value reference 176. The white-value reference 172 and the black-value reference 176 can be used during the evaluation for calibrating and/or adjusting optical signals which originate from these references (e.g. reflection signals from light beams reflected at these regions). This renders it possible, for example, to set absolute-value levels of "high" signals and "low" signals, or the ratio between these. By way of example, this can be used to set appropriate thresholds, by means of which low modules 146 and high modules 148 can be identified in appropriate measurements by comparing signal levels to these thresholds. The barcode 110 can also be read by commercial readers in the exemplary embodiment as per FIG. 9.

Figure 10:
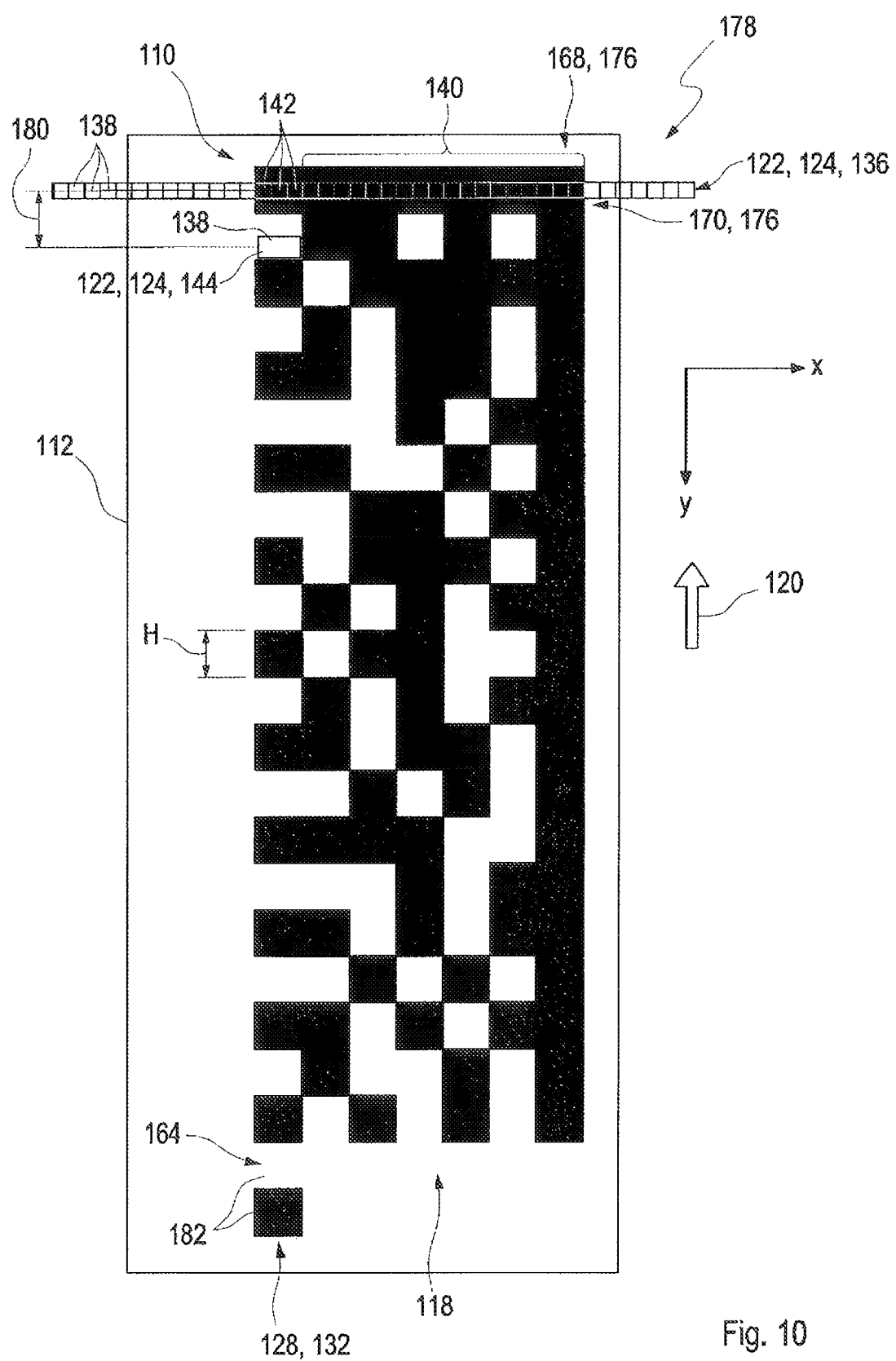
FIG. 10 shows a modification of the barcode as per FIG. 9, in which the clock track is extended by one module and in which the clock track itself can be used as reference track by means of an additional reference detector.

FIG. 10 illustrates a further exemplary embodiment of a barcode 110. In this exemplary embodiment, the barcode 110 can, in an exemplary fashion, substantially correspond to a commercially available two-dimensional barcode. Once again, provision is made for an information field 118 which, in an exemplary fashion, has an embodiment that is analog to the information field 118 as per the exemplary embodiment in FIG. 9. However, in principle, other embodiments are also possible.

The barcode 110 once again has an information field 118. A clock track 128 is integrated into this information field 118 in an exemplary fashion. However, in principle, a separate embodiment of the clock track 128, for example analogously to the exemplary embodiment in FIG. 1, is also possible, with an optional quiet zone 164 between the information field 118 and the clock track 128.

However, in contrast to the preceding embodiments, the barcode 110 as per FIG. 10 does not have a separate reference track 132. Rather, use is made of the second afore-mentioned option for producing phase-offset clock track signals and reference signals, namely the option of using the clock track 128 itself as a reference track 132 by using a reference detector 144 which is spatially offset in the y-direction compared to the clock track detector 142. Accordingly, a device 178 for transmitting at least one item of information is illustrated in an exemplary and very schematic fashion in FIG. 10, in a similar illustration as already shown previously in FIG. 2 or in FIG. 6, which comprises a bar-code reader 124 and a carrier 112 with a barcode 110.

As explained above, no separate reference track 132 is provided in the barcode 110; rather, the clock track 128 is simultaneously used as reference track 132. Here, a phase shift between the clock track signals and the reference track signals is achieved by virtue of the fact that the reference detector 144 is spatially offset compared to the clock track detector 142 by an offset 180 in the y-direction. This is equivalent to a phase-shift in position space. By way of example, the phase shift can be a non-even multiple of the module height H, for example an offset $$\Delta = n \cdot 2 \cdot H + \frac{1}{2} \cdot H.$$

Accordingly, this results in a phase shift of, for example, 90° with respect to a period P=2·H. Here n is an integer.

A problem which may occur in the case of conventional barcodes 110 when the end of the barcode 110, i.e. the lower end in FIG. 10, is reached is that of the clock track 128 having an embodiment which is too short. It is for these reason that the clock track 128 may be extended beyond the information field 118 in the movement direction 120 in this or else in other exemplary embodiments of a barcode 110 according to the invention, in which the clock track 128 is simultaneously also used as reference track 132, with a reference detector 144 spatially offset with respect to the clock track detector 142; this is brought about by virtue of one or more additional clock modules 182 being provided, which, in the y-direction, extend beyond the spatial limit of the information field 118. This can also be realized in such a way that the demand for a quiet zone 164 of at least one module around the information field 118 can be met. This is why the barcode 110, in the embodiment as per FIG. 10, can, in principle, also be read by commercially available detectors 122.

In principle, the spatial offset in the y-direction between the reference detector 144 and the clock track detector 142 can be realized in various ways. This is indicated in FIG. 10. Here, for example, use can once again be made of a row detector 136. By way of example—like in the other exemplary embodiments as well—this can be realized by virtue of the fact that use is made of a two-dimensional detector field with optical sensors 138 arranged in a two-dimensional fashion, of which merely one row is used as row detector 136. However, in principle, the use of a pure single-row detector is also possible. In order to realize the reference detector 144 offset in the y-direction, use can then be made of a further detector, for example a single, spatially offset detector. However, as an alternative or in addition thereto, use can also be made of one or more optical sensors 138 of a two-dimensional sensor arrangement which differs from the row of the row detector 136.

In the exemplary embodiment as per FIG. 10, the reference detector 144 is, in an exemplary fashion, merely offset in the y-direction compared to the clock track detector 142. However, this is not necessarily the case, as shown in an exemplary fashion on the basis of FIG. 11. Here, the at least one reference detector is not only offset in the y-direction by the offset 180 but also, in an exemplary fashion, offset by one module in the x-direction. Here, the clock track 128, as illustrated in FIG. 11, can optionally also be widened in the x-direction, for example by an additional module.

Figure 11:
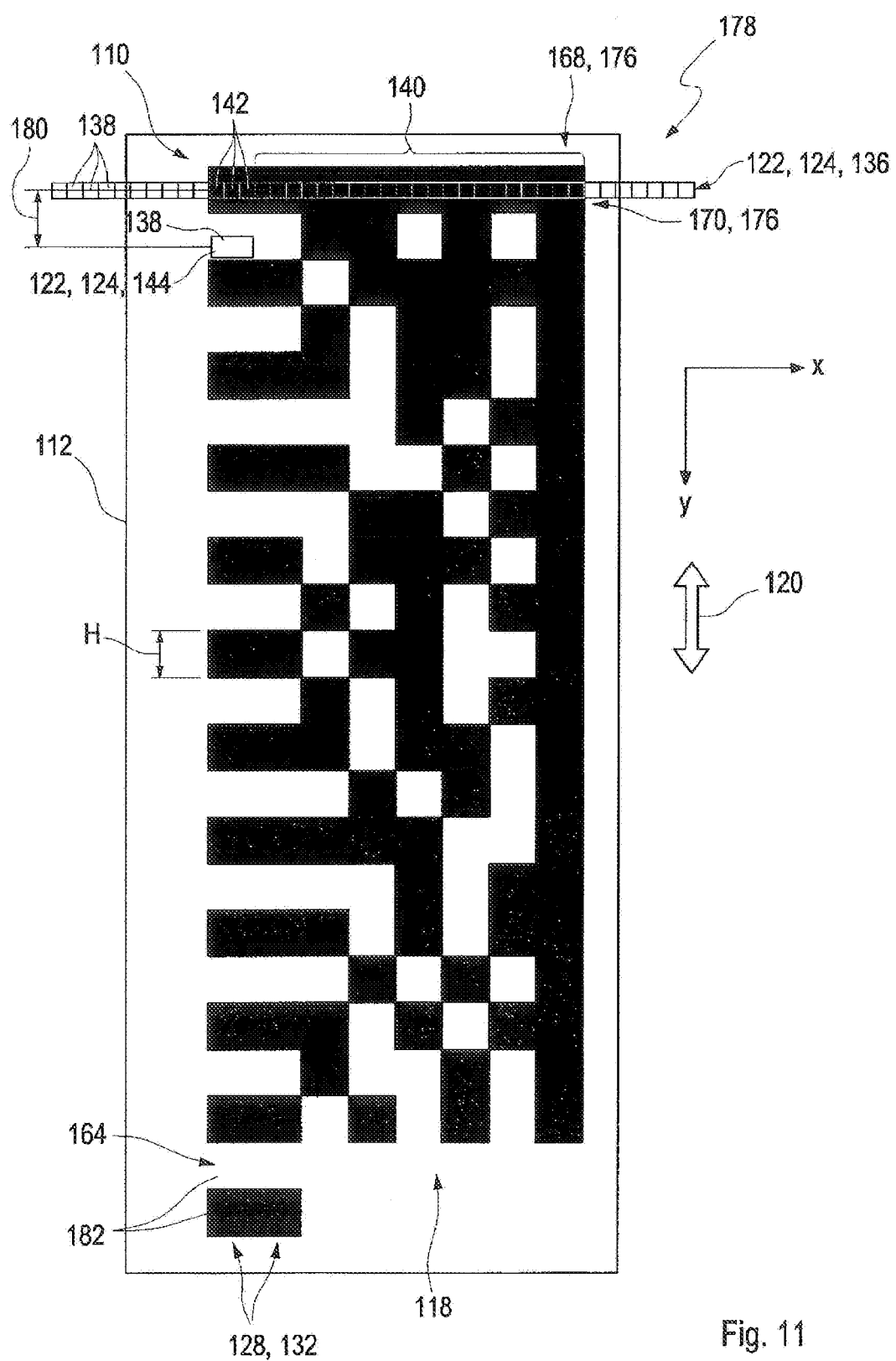
FIG. 11 shows an alternative embodiment of the barcode as per FIG. 10, in which the clock track was extended in a lateral direction with respect to the reading direction.

FIGS. 12a and 12b show, in a plan view (FIG. 12a) or in a view from the side (FIG. 12b), an exemplary embodiment of a barcode reader 124 which can, for example, be used in the device 178 as per FIG. 11. In this exemplary embodiment, the barcode reader 124 can more particularly be embodied as optical contact reader 184 such that the carrier 112 with the barcode 110 and the barcode reader 124 (see FIG. 12b) together can have a height h which, for example, is no more than 10 mm, typically no more than 5 mm.

What is shown in the exemplary embodiment illustrated in FIGS. 12a and 12b is that all detectors 140, 142 and 144, can also be wholly or partly embodied with the same design, provided that use is made of a suitable optical unit. In this exemplary embodiment, the detectors 140, 142 and 144 use one and the same sensor row 186 of a detector 122 in an exemplary fashion. This sensor row 186 can in turn, analogously to e.g. FIG. 11, comprise a plurality of optical sensors 138 (not illustrated in FIGS. 12a and 12b), for example at least one optical sensor 138 per module 116 or 130 or 134 of the barcode 110. The module width of the modules in the x-direction typically is an integer multiple of the width of the optical sensors 138; in principle, this can also apply to all other exemplary embodiments.

In the exemplary embodiment illustrated in FIGS. 12a and 12b, the barcode reader 124 embodied as optical contact reader 184 has one or more illumination units 188, by means of which the barcode 110 can be illuminated. By way of example, the illumination 188 can be realized by means of one or more light-emitting diodes, rows of light-emitting diodes, incandescent lamps or other types of illumination apparatuses. In particular, as indicated in FIGS. 12a and 12b, use can be made of a row-shaped illumination or a plurality of individual light sources can be arranged in one or more rows.

In this exemplary embodiment, the illumination 188 is subdivided into a code illumination 190 and a reference illumination 192, which is arranged offset compared to the code illumination 190 by an offset in the y-direction. The code illumination serves to illuminate the information field 118, optionally including the clock track 128, whereas the reference illumination 192 serves to illuminate the reference track 132. However, other embodiments are also possible, and so, for example, provision can additionally be made for a clock illumination or the reference illumination 192 can else be integrated into the code illumination 190.

The light emitted by the illumination 188 is reflected on the barcode 110 in accordance with the reflection properties of the modules 116, 130, 134. The reflected light is received by the barcode reader 124 again. This can be brought about directly, or through "windows", through which the reflected light can reenter the barcode reader 124. In FIGS. 12a and 12b such windows are illustrated optionally in the form of code windows 194 for the reflected light from the code illumination 190 and in the form of reference windows 196 for the reflected light from the reference illumination 192. By way of example, these windows 194, 196 can be embodied as real openings in a surface of the barcode reader 124 facing the barcode 110 or can also be simple virtual entry regions of the respective reflected beams. At the same time, these reference windows 196 or code windows 194 can represent the virtual or real location of the respective detectors, i.e., for example, the code window 194 can represent the respective location of the barcode detectors 140 and/or clock track detectors 142 and the location of the reference window 196 can represent the location of the reference detectors 144. Accordingly, the distance in the y-direction between the code window 194 and the reference window 196 can for example correspond to the offset 180 as per the embodiments in FIGS. 10 and 11. Alternatively, the spacing of the code illumination 190 from the reference illumination 192 in the y-direction could also be considered as the offset 180.

In the illustrated exemplary embodiment as per FIGS. 12a and 12b, provision is furthermore made for an imaging optical unit 198 as optional element. This imaging optical unit 198 can be embodied to guide and/or image those reflected beams from regions of the barcode 110 positioned over the respective windows 194, 196 onto the respective sections of the sensor row 186. To this end, the imaging optical unit 198 can for example comprise one or more deflection elements 200. In FIG. 12b, these deflection elements 200 are embodied as prisms in an exemplary fashion. However, as an alternative or in addition thereto, one or more of the deflection elements 200 can be embodied in a different form, for example in the form of mirrors or similar deflection elements known to a person skilled in the art. In the illustrated exemplary embodiment, provision is made for code deflection elements 202 for deflecting the reflected light beams originating from the code illumination 190, and for reference deflection elements 204 for deflecting the reflected light beams originating from the reference illumination 192 in the horizontal direction. Furthermore, sensor deflection elements 206 are provided above the sensor row 186 for guiding the light beams onto the sensor row 186.

Furthermore, the imaging optical unit 198 can comprise one or more optical waveguide elements and/or imaging elements. By way of example, this can be combined optical waveguide/lens elements, for example in the form of so-called rod lenses, which are de-noted by reference sign 208 in FIGS. 12 and 12b. By way of example, provision can be made for respectively one or more of such rod lenses 208 in the x-direction per module 114 to be detected. By way of example, the rod lenses 208 can be embodied as so-called gradient index lenses.

An optical contact reader 184, in particular, can be represented by means of the optional embodiments of the barcode reader 124 as per FIGS. 12a and 12b. By way of example, said optical contact reader is described by an offset beam input, respectively having the windows 194 and 196 and the additional optical sensor element in the form of the reference detector 144. The code window 194 is imaged on the optical sensor row 186 by means of the code illumination 190 and via the associated imaging optical unit 196. The reference window 196 is in turn illuminated by the reference illumination 192 and likewise imaged onto another portion of the same optical sensor row 186 via the associated imaging optical unit 198.

Figure 13:
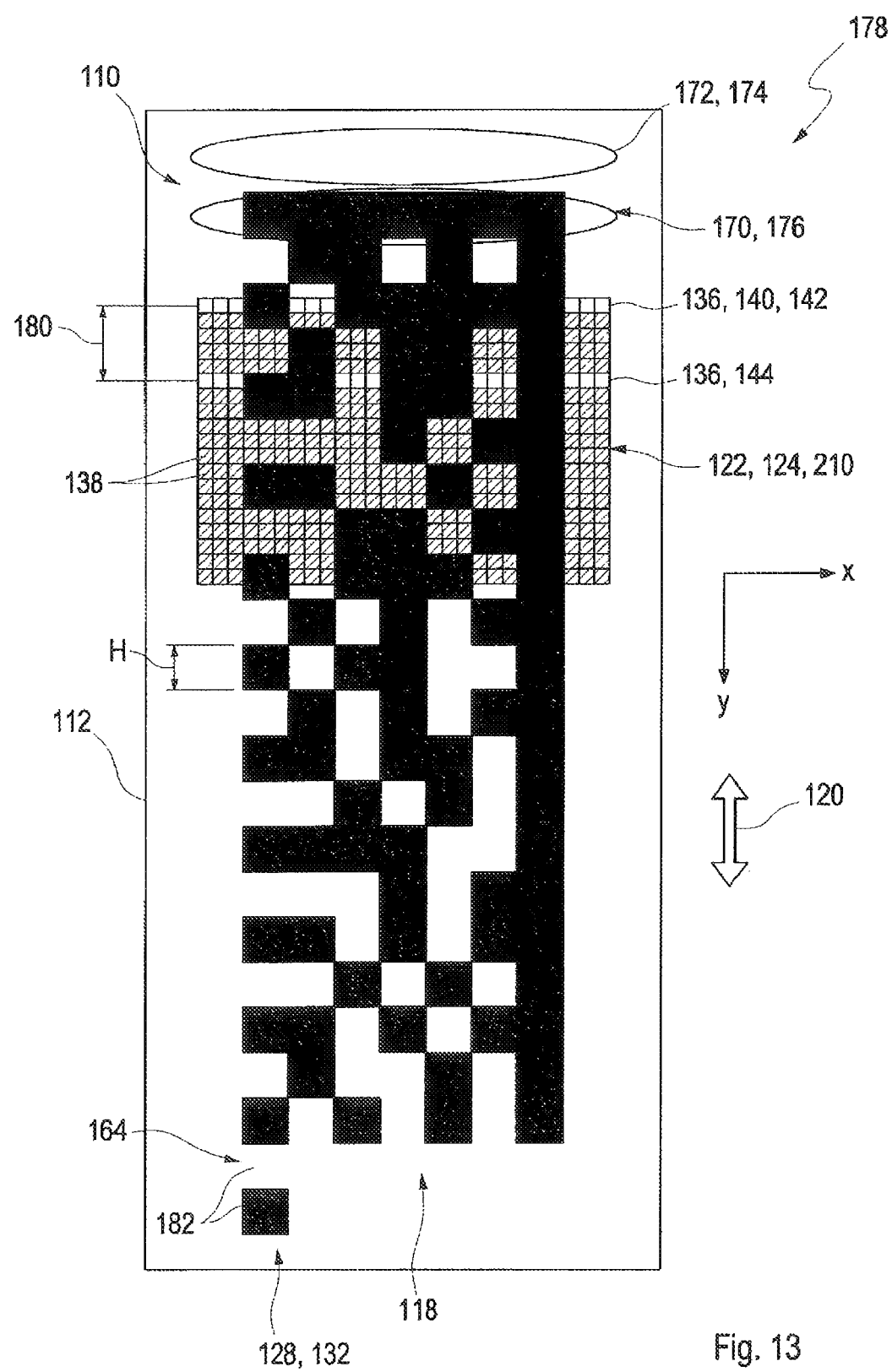
FIG. 13 shows a barcode and a barcode reader in the form of an optical two-dimensional sensor, of which two phase-shifted rows are used.

FIG. 13 illustrates a further exemplary embodiment of a device 178 according to the invention, a barcode reader 124 and a barcode 110 on a carrier 112, in which the barcode reader 124 has an alternative embodiment to the exemplary embodiment illustrated in FIG. 10. In this exemplary embodiment, the detector 122 comprises an optical field sensor 210 with a plurality of optical sensors 138 aligned in two dimensions (parallel to the x-axis and parallel to the y-axis). Two sensor rows (i.e. respectively sensors with the same y-coordinate) from this field sensor 210 are used as row detectors 136, which sensor rows have an offset 180 in the y-direction with respect to one another. By way of example, the optical field sensor 210 can be a CCD camera chip and/or a cost-effective mouse sensor. While the upper row detector 136 can, for example, analogously to the description of FIG. 10, provide the barcode detector 140 and the clock track detector 142, the lower one of the row detectors 136 in FIG. 13 provides the reference detector 144. As an alternative to this two-row embodiment, it is also possible to use further rows. The offset 180 of the row detectors 136 can, for example, once again be selected analogously to the offset 180 as per FIG. 10. By way of example, it is possible to select an offset which satisfies the condition $$n \cdot H + \frac{1}{2} \cdot H,$$

where n can in turn be an integer. By way of example, this offset can correspond to a phase shift of 90° in relation to a period of 2H or of 180° in relation to a period H.

Figure 14:
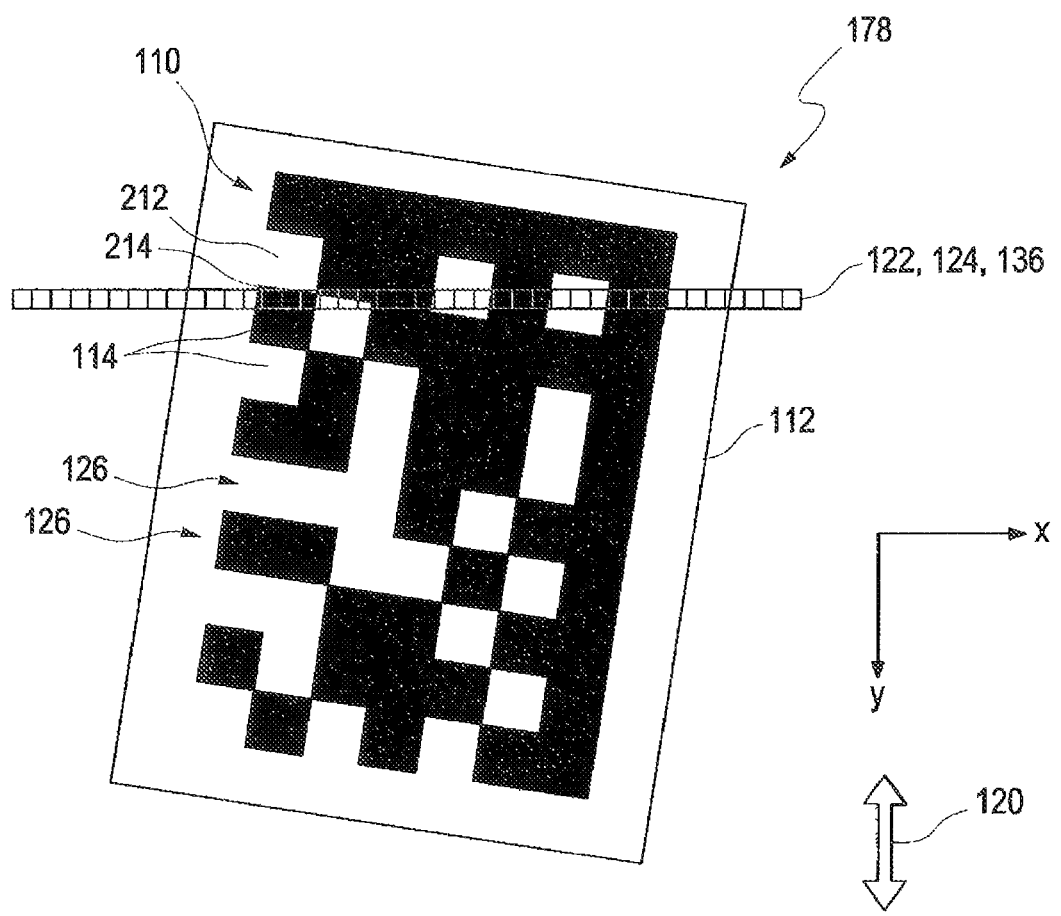
FIG. 14 shows an explanation of the problem of reading errors if the barcode and the carrier thereof are inserted with an angle offset into a barcode reader.

A barcode reader 124 which is embodied as push-type or pull-type reader, i.e. as a bar-code reader 124 in which the carrier 112 is moved relative to the detector 122, typically requires a certain amount of headroom in respect of the movement of the carrier 112. This is illustrated in an exemplary fashion in FIG. 14. As a result of this headroom, there can be an angle offset between the rows 126 and the x-axis, which is aligned perpendicular to the movement direction 120. This is expressed by virtue of the fact that a code-module intended value 212, i.e. that module 114 which should in actual fact be read out, deviates from a code-module actual value 214. By way of example, in FIG. 14, the code-module intended value 212 in the form of a white or high representation is erroneously reproduced by the row detector 136 as code-module actual value 214 in the form of a black or low representation.

Figure 15:
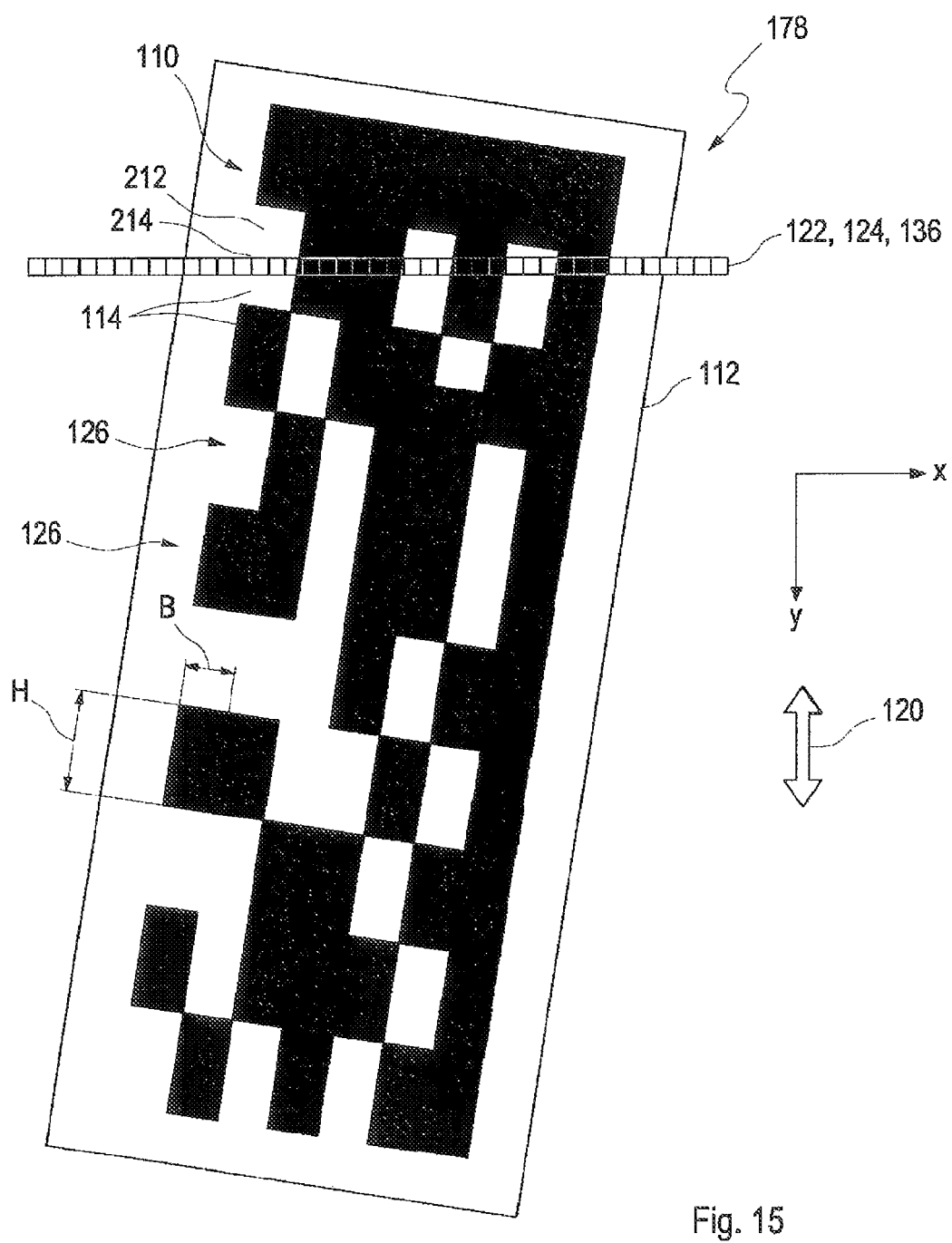
FIG. 15 shows a solution to the angle offset problem as per FIG. 14 by extending the code modules of the barcode in the push or pull direction.

This error can be reduced by virtue of the fact that the modules 114 are completely or partly modified in terms of their height-to-width ratio. Thus, the module height H can be increased compared to the module width B. This is illustrated in FIG. 15 in an exemplary fashion. As is possible to identify on the basis of FIG. 15, the code-module intended value 212 corresponds to the code-module actual value 214, at least in the case of an approximately central read-out of the modules 114.

Figure 17:
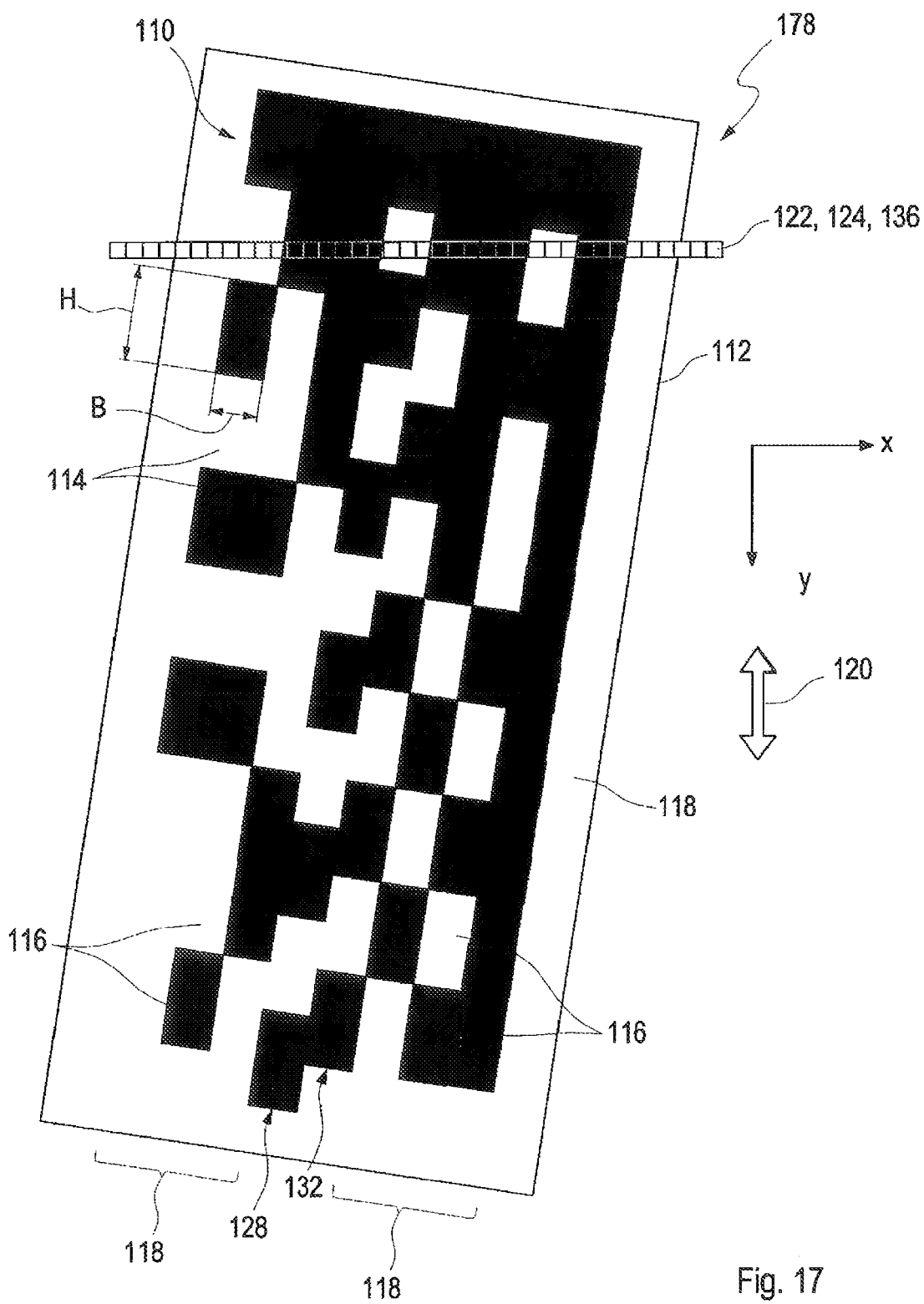
FIG. 17 shows an exemplary embodiment of a barcode, as an alternative to FIG. 15, with a clock track situated inside and an optional reference track situated inside.

FIG. 17 illustrates an exemplary embodiment of a barcode 110 and a device 178 which is an alternative to the one in FIG. 15. In principle, the barcode 110 can have an analogous embodiment to FIG. 15, for example. However, alternatively, other exemplary embodiments can also be modified as per the concept illustrated in FIG. 17. The barcode 110 in FIG. 17 takes account of the discovery that the error due to an angle offset, described on the basis of FIG. 14, naturally has the smallest effect on the center of the barcode 110 with respect to a direction perpendicular to the movement direction 120. Accordingly, it is proposed in the exemplary embodiment as per FIG. 17 to move the clock track 128 and/or the optional reference track 132 into the center of the barcode 110. This means that the clock track 128 and optionally the reference track 132 are surrounded by information modules 116 and information fields 118 on both sides if one direction is perpendicular to the movement direction 120, i.e. that respectively at least one column of information modules 116 adjoins the clock track 128 and, optionally, the reference track 132 on both sides. Since the clock track 128 and, optionally, the reference track 132 are responsible for the time of capturing the module information, the exemplary embodiment as per FIG. 17 with the step of moving the tracks 128 and, optionally, 132 into the code center offers the advantage of precise referencing. The smallest effect of an angle offset is naturally expected in the center of the code.

In principle, the exemplary embodiment as per FIG. 17 can be transferred to other exemplary embodiments of the present invention. Thus, the concept of FIG. 15 that the modules 114 are elongate in the movement direction 120, i.e. have a module height H which exceeds a module width B, is implemented in FIG. 17 in an exemplary fashion. However, alternatively, other embodiments are also possible, for example embodiments with square modules. Furthermore, the reference track 132 is not necessarily required because, for example analogously to FIG. 11, a phase offset can, alternatively or additionally, also be created by the detector 122. Furthermore, it is not mandatory for the clock track 128 and the reference track 132 to be arranged next to one another; rather, information modules 116, for example, can also be situated between these tracks 128, 132. Various other embodiments are possible.

Figure 16:
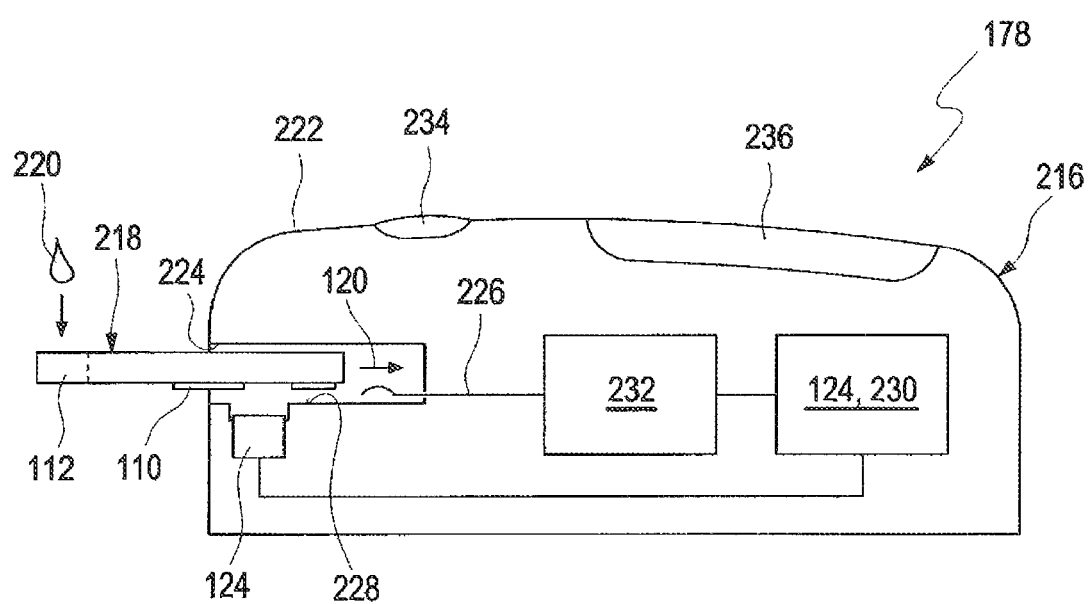
FIG. 16 shows an exemplary embodiment of a device according to the invention in the form of a medical measuring instrument with a medical consumable in the form of a test strip.

FIG. 16 finally illustrates a possible exemplary embodiment of a device 178 according to the invention in a schematic sectional illustration. In this exemplary embodiment 216, the device comprises, in an exemplary fashion, a medical measuring instrument, which can, for example, be embodied as blood glucose measuring instrument, and which is configured to interact with a medical consumable article 218, for example a test strip for analyzing a liquid sample 220. The test strip itself comprises a strip-shaped carrier 212, on which, for example, one or more test fields are applied; said test fields are not illustrated in FIG. 16 and for example comprise one or more test chemicals for qualitative and/or quantitative detection of at least one analyte in the sample 220.

By way of example, the device 178 can comprise a housing 222, in which provision is made for at least one receptacle 224 for receiving the carrier 212 or the medical consumable article 218. By way of example, this receptacle 224 can comprise a receptacle slot. By way of example, provision can also be made in this receptacle 224 for at least one electric contact 226 for electrically contacting the medical consumable article 218 at one or more contact surfaces 228. This embodiment is feasible, particularly when using electrochemical test strips as medical consumable articles 218. However, as an alternative or in addition thereto, these can also, for example, be test strips which can be read out optically. By way of example, in this case the electric contacts 226 can be replaced by an optical reader, for example an optical reader which is configured to read out color changes, which can be traced back to the analyte, in one or more test fields.

Furthermore, the device 178 in the exemplary embodiment illustrated in FIG. 16 comprises one or more barcode readers 124 which are configured for reading out a barcode 110 which is inserted into the receptacle 224 in a movement direction 120. In respect of the possible embodiments of the barcode reader 124, reference can be made to the above-described embodiments or to other possible embodiments within the scope of the present invention. By way of example, the barcode reader 124 can be connected to a central control unit 230. However, as an alternative or in addition thereto, components of the barcode reader 124 can also be implemented in the central control unit 230 and/or in other parts of the device 178. Thus, for example, merely an optical component of the barcode reader 124 can be arranged in the region of the receptacle 224, whereas data storage and/or evaluation devices of the barcode reader 124 can be wholly or partly implemented in the central control unit 230. Thus, for example, one or more evaluation de-vices of the barcode reader 124 can be implemented in the central control unit 230 as software or hardware components. By way of example, the central control unit 230 can comprise a data processing device, optionally with one or more volatile or non-volatile storage elements. Moreover, the device 178 can also comprise further components, for example an evaluation device 232 which can, for example, be configured to carry out the actual measurement of the device 178, for example analyte detection. However, this evaluation device 232 can also be wholly or partly implemented in the central control unit 230. The central control unit 230 can be embodied as a single component, or else it can be embodied in a number of parts, optionally also distributed over various regions of the device 178. Furthermore, the device 178 can comprise one or more operating elements 234, for example for entering commands and/or control data and/or other information, and/or one or more display devices 236, for example one or more displays. In principle, provision can also be made for other types of user interfaces.

In the device, illustrated in an exemplary fashion in FIG. 16, with the medical measuring instrument 216 and the medical consumable article 218, for example an analytic test element 238, the medical consumable article 218 with the barcode 110 is typically inserted into the receptacle 224 by hand such that a purely manual advance is present. In this case, it is particularly expedient to use a barcode reader 124 embodied according to the invention. As illustrated above, the barcode reader 124 can, in particular, be embodied in such a way that, during the movement of the carrier 112 in or against the movement direction 120, the barcode 110 is read out row-by-row by means of one or more detectors 122 in the form of one or more row detectors 136. In this case, the method proposed above can be noticed in a particularly advantageous fashion as a result of the stability of the above-described method and the above-described device 178 in respect of possible irregularities during the advance, in particular during the manual advance.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A device for transmitting at least one item of information, the device comprising:
    at least one barcode reader for capturing a barcode connected to a moved carrier, wherein the barcode reader comprises:
        at least one optical barcode detector for at least one-dimensional capture of information modules of the barcode, at least one optical clock track detector for capturing clock track modules of a clock track of the barcode, and at least one optical reference detector for capturing at least one item of reference information from the barcode, wherein the barcode reader is configured to deduce a movement direction of the carrier from at least one signal from the at least one optical clock track detector and at least one signal from the at least one optical reference detector, wherein the device further comprises the at least one carrier with the at least one barcode, wherein the barcode comprises:

a plurality of information modules, at least one clock track, wherein the at least one clock track has a plurality of successive clock track modules arranged successively along a straight or curved line in the barcode and which do not simultaneously serve as information modules of the barcode but which only serve as a clock when the barcode is moved relative to the barcode reader, and at least one reference track, wherein the at least one reference track comprises a second clock track, and wherein the at least one reference track has the same periodicity as the at least one clock track and has a spatial phase shift compared to the at least one optical clock track.

2. The device as claimed in claim 1, wherein the barcode reader is configured to capture at least one signal change caused by the at least one clock track in the signal from the at least one optical clock track detector.

3. The device as claimed in claim 2, wherein the signal change caused by the clock track in the signal from the clock track detector is a positive or negative edge.

4. The device as claimed in claim 1, wherein the barcode reader is configured to deduce the movement direction from a sign of a signal change captured by the at least one optical clock track detector and an absolute value of the signal from the at least one optical reference detector.

5. The device as claimed in claim 4, wherein the barcode reader is configured to deduce a first movement direction if either (i) a negative edge is identified in the signal from the at least one optical clock track detector and a first signal level is identified in the signal from the at least one optical reference detector, or (ii) a positive edge is identified in the signal from the at least one optical clock track detector and a second signal level is identified in the signal from the at least one optical reference detector, and wherein the barcode reader is further configured to deduce a second movement direction in the opposite direction to the first movement direction if either (iii) a positive edge is identified in the signal from the at least one optical clock track detector and the first signal level is identified in the signal from the at least one optical reference detector, or (iv) a negative edge is identified in the signal from the at least one optical clock track detector and the second signal level is identified in the signal from the at least one optical reference detector.

6. The device as claimed in claim 4, wherein the absolute value of the signal from the reference detector is a coincident signal from the reference detector.

7. The device as claimed in claim 1, furthermore comprising a data storage, wherein the barcode reader is configured to read out information contained in rows of the barcode and store it in the data storage, respectively with an address counter corresponding to the row, wherein the barcode reader is configured to increase or decrease the address counter incrementally in accordance with the identified movement direction.

8. The device as claimed in claim 1, wherein the at least one optical clock track detector is part of the barcode detector.

9. The device as claimed in claim 1, wherein the at least one optical reference detector is arranged with respect to the at least one optical clock track detector next to the at least one optical clock track detector in a direction perpendicular to the movement direction.

10. The device as claimed in claim 1, comprising at least one optical sensor element, wherein the at least one optical clock track detector and the at least one optical reference detector are configured to use the at least one optical sensor element.

11. The device as claimed in claim 10, wherein the optical sensor element comprises a sensor row.

12. The device as claimed in claim 1, wherein the optical reference information is selected from: optical information from a reference track of the barcode; and optical information from the clock track of the barcode at a predetermined offset from current optical information from the clock track read out by the at least one optical clock track detector.

13. The device as claimed in claim 12, wherein the optical reference is optical information from the clock track of the barcode at a predetermined offset from current optical information from the clock track read out by the clock track detector, wherein the predetermined offset deviates from an even multiple of a module height of the clock track.

14. The device as claimed in claim 1, further comprising a receptacle for receiving the carrier, wherein the receptacle is configured to enable movement of the carrier relative to the barcode reader, wherein the barcode reader is configured such that the barcode can be read out by means of the barcode reader while the carrier moves in the receptacle.

15. The device as claimed in claim 1, wherein the at least one clock track has a plurality of periodically alternating clock track modules, wherein the alternating clock track modules are configured to produce at least two different signal levels alternately in the at least one optical clock track detector when passing the at least one optical clock track detector.

16. The device as claimed in claim 1, wherein the barcode is a two-dimensional barcode.

17. The device as claimed in claim 1, wherein the at least one reference track is arranged parallel to the movement direction.

18. The device as claimed in claim 1, wherein the at least one reference track has a plurality of periodically alternating reference track modules, wherein the alternating reference track modules are configured to produce at least two different signal levels alternately in the at least one optical reference detector when passing the at least one optical reference detector, wherein a periodicity of the at least one reference track is phase-shifted compared to a periodicity of the at least one clock track.

19. The device as claimed in claim 1, wherein the at least one reference track is aligned parallel to the at least one clock track.

20. The device as claimed in claim 1, wherein modules of the barcode have a module height in the movement direction and a module width perpendicular to the movement direction, wherein the module height exceeds the module width.

21. The device as claimed in claim 20, wherein the module height exceeds the module width by at least a factor of 1.2.

22. The device as claimed in claim 20, wherein the module height exceeds the module width by at least a factor of 1.5.

23. A method of transmitting at least one consumable article-specific information, comprising transmitting the consumable article-specific information from at least one medical consumable article to a medical instrument interacting with the medical consumable article by using the device of claim 1.

24. The method as claimed in claim 23, wherein the medical instrument interacting with the medical consumable article is selected from the group consisting of a medical measuring instrument and a therapy instrument.

25. The device as claimed in claim 1, wherein the phase shift is a predetermined deviation from a module height H of the clock track modules.

26. The device as claimed in claim 25, where the phase shift is a non-even multiple of H/2.

27. A method for capturing an optical barcode connected to a moving carrier, the method comprising:
    capturing information modules of the barcode at least one-dimensionally; and
    capturing clock track modules of a clock track of the barcode using at least one clock track detector,
    wherein at least one item of reference information from the barcode is captured by means of at least one reference detector, wherein a movement direction of the carrier is deduced from at least one signal from the clock track detector and at least one signal from the reference detector, wherein the clock track has a plurality of successive clock track modules arranged successively along a straight or curved line in the barcode and which do not simultaneously serve as information modules of the barcode but which only serve as a clock when the barcode is moved relative to the barcode reader, wherein the barcode furthermore has at least one reference track, wherein the reference track is embodied as second clock track, and wherein the reference track has the same periodicity as the clock track and has a spatial phase shift compared to the clock track.

* * * * *